United States Patent
Acharya et al.

(10) Patent No.: US 9,585,958 B2
(45) Date of Patent: Mar. 7, 2017

(54) COMPOSITIONS AND METHODS FOR REDUCING LACTATE LEVELS

(71) Applicant: The Regents of the University of California, Oakland, CA (US)

(72) Inventors: Abhinav P. Acharya, El Cerrito, CA (US); Niren Murthy, Berkeley, CA (US); Elliot C. Woods, Berkeley, CA (US)

(*) Notice: Subject to any disclaimer, the term of this patent is extended or adjusted under 35 U.S.C. 154(b) by 0 days.

(21) Appl. No.: 14/491,714

(22) Filed: Sep. 19, 2014

(65) Prior Publication Data

US 2015/0105348 A1 Apr. 16, 2015

Related U.S. Application Data

(60) Provisional application No. 61/881,898, filed on Sep. 24, 2013.

(51) Int. Cl.
*C07F 5/02* (2006.01)
*A61K 31/69* (2006.01)
*A61K 45/06* (2006.01)

(52) U.S. Cl.
CPC .............. *A61K 45/06* (2013.01); *A61K 31/69* (2013.01)

(58) Field of Classification Search
None
See application file for complete search history.

(56) References Cited

U.S. PATENT DOCUMENTS

2011/0190235 A1* 8/2011 Chen ................. C07F 5/025
514/64

FOREIGN PATENT DOCUMENTS

WO WO 2007095638 A2 * 8/2007 ............. A62K 31/69

OTHER PUBLICATIONS

Bankir et al., "New Insights into Urea and Glucose Handling by the Kidney, and the Urine Concentrating Mechanism", Kidney Int., 2012, 81(12):1179-1198.
Fall et al., "Lactic Acidosis: From Sour Milk to Septic Shock", Journal of Intensive Care Medicine, 2005, 20:255-271.
Ferriero et al., "Phenylbutyrate Therapy for Pyruvate Dehydrogenase Complex Deficiency and Lactic Acidosis", Science Translational Medicine, 2013, 5:175ra31.
Fraley et al., "Stimulation of Lactate Production by Administration of Bicarbonate in a Patient with a Solid Neoplasm and Lactic Acidosis", The New England Journal of Medicine, 1980, 303:1100-1102.
Kette et al., "Buffer Agents do not Reverse Intramyocardial Acidosis During Cardiac Resuscitation", Circulation, 1990, 81:1660-1666.
Luft et al., "Definition of Clinically Relevant Lactic Acidosis in Patients with Internal Diseases", American Journal of Clinical Pathology, 1983, 80(4):484-489.
Ritter et al., "Paradoxical Effect of Bicarbonate on Cytoplasmic pH", Lancet, 1990, 335:1243-1246.
Sartain, et al., "Complexation of l-Lactate with Boronic Acids: A Solution and Holographic Analysis", Chem. Eur. J., 2008, 14:4060-4067.
Stacpoole et al., "A Controlled Clinical Trial of Dichloroacetate for Treatment of Lactic Acidosis in Adults. The Dichloroacetate-Lactic Acidosis Study Group", The New England Journal of Medicine, 1992, 327:1564-1569.
Weil et al., "Difference in Acid-Base State Between Venous and Arterial Blood During Cardiopulmonary Resuscitation", The New England Journal of Medicine, 1986, 315:153-156.

\* cited by examiner

*Primary Examiner* — Michael Barker
(74) *Attorney, Agent, or Firm* — Bozicevic Field & Francis, LLP; Paula A. Borden; Glenn J. Foulds

(57) ABSTRACT

The present disclosure provides methods of reducing levels of lactate in a fluid or tissue in an individual. The present disclosure provides pharmaceutical compositions suitable for use in the methods.

23 Claims, 7 Drawing Sheets

COMPOSITIONS AND METHODS FOR REDUCING LACTATE LEVELS

CROSS-REFERENCE

This application claims the benefit of U.S. Provisional Patent Application No. 61/881,898, filed Sep. 24, 2013, which application is incorporated herein by reference in its entirety.

STATEMENT REGARDING FEDERALLY SPONSORED RESEARCH

This invention was made with government support under Grant Nos. HL096796 and AI088023 awarded by the National Institutes of Health. The government has certain rights in the invention.

INTRODUCTION

Elevated blood lactate is a central problem in intensive care units, and causes millions of deaths annually, due its numerous physiologic effects, such as reducing blood pH and blood pressure, globally changing enzyme activity, and inducing apoptosis. Although, bicarbonate treatment can suppress the pH drop caused by elevated lactate, it is still not an effective therapy, because of its toxic side effects, and inability to reduce lactate levels, the root cause of lactic acidosis.

LITERATURE

Luft et al., Am J Clin Pathol. 1983 October; 80(4):484-9; Fall et al., J Intensive Care Med. 2005 September-October; 20(5):255-71; Bankir et al., Kidney Int. 2012 June; 81(12):1179-98. doi: 10.1038/ki.2012.67. Epub 2012 Mar. 28; Ferriero et al., Sci Transl Med. 2013 Mar. 6; 5(175):175ra31; Stacpoole et al., N Engl J Med. 1992 Nov. 26; 327(22):1564-9; Fraley et al., N Engl J Med. 1980 Nov. 6; 303(19):1100-2; Weil et al., N Engl J Med. 1986 Jul. 17; 315(3):153-6; Ritter et al., Lancet. 1990 May 26; 335(8700):1243-6; Kette et al., Circulation. 1990 May; 81(5):1660-6; and Sartain et al., Chemistry. 2008; 14(13):4060-7.

SUMMARY

The present disclosure provides methods of reducing levels of lactate in a fluid or tissue in an individual. The present disclosure provides pharmaceutical compositions suitable for use in the methods.

Features

The present disclosure provides a pharmaceutical composition, comprising:
a) a compound of formula I:

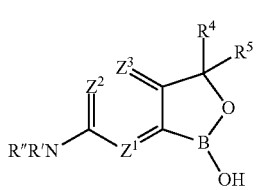

wherein $Z^1$ is CH, $CR^1$ or N;
$Z^2$ is CH, $CR^2$ or N;
$Z^3$ is CH, $CR^3$ or N;
$R^1$, $R^2$, $R^3$, $R^4$ and $R^5$ are each independently selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl; and
R' and R" are each independently selected from hydrogen, an alkyl, an aryl, substituted alkyl and substituted aryl, and acyl; and
b) a pharmaceutically acceptable excipient.

The present disclosure provides a pharmaceutical composition, comprising:
a) a compound of formula II:

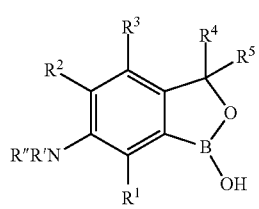

wherein $R^1$, $R^2$, $R^3$, $R^4$ and $R^5$ are each independently selected from hydrogen, acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO—alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl; and
R' and R" are each independently selected from hydrogen, an alkyl, an aryl, substituted alkyl and substituted aryl, and acyl; and
b) a pharmaceutically acceptable excipient.

The present disclosure provides a pharmaceutical composition, comprising:
a) a compound of formula III:

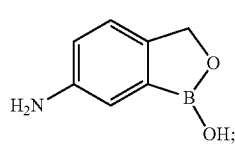

and
b) a pharmaceutically acceptable excipient.

The present disclosure provides a method of reducing the level of lactate in a fluid or tissue of an individual, the method comprising administering to the individual an effective amount of:

a) a compound of formula I:

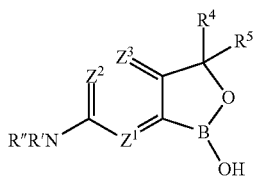

(I)

wherein $Z^1$ is CH, $CR^1$ or N;
$Z^2$ is CH, $CR^2$ or N;
$Z^3$ is CH, $CR^3$ or N;
$R^1$, $R^2$, $R^3$, $R^4$ and $R^5$ are each independently selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl; and R' and R" are each independently selected from hydrogen, an alkyl, an aryl, substituted alkyl and substituted aryl, and acyl;

b) a compound of formula II:

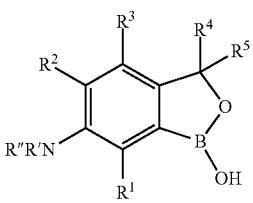

(II)

wherein $R^1$, $R^2$, $R^3$, $R^4$ and $R^5$ are each independently selected from hydrogen, acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl; and R' and R" are each independently selected from hydrogen, an alkyl, an aryl, substituted alkyl and substituted aryl, and acyl;

c) a compound of formula III:

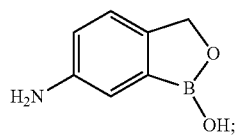

(III)

or d) a pharmaceutical composition comprising a compound of (a), (b), or (c), wherein said administering reduces the level of lactate in a fluid or tissue in the individual. In some cases, the fluid is blood or a blood fraction. In some instances, the individual is a mammal. For example, in some instances, the individual is a human. In some embodiments, an effective amount of the boronic acid compound is in a range of from 10 μM to 500 mM. In some cases, the compound is administered in a total daily dose of from 0.1 mg to 500 mg. In some embodiments of a subject method, administering the compound or pharmaceutical composition reduces the level of lactate in a fluid or tissue in the individual by at least 5%. In some embodiments of a subject method, administering the compound or pharmaceutical composition reduces the level of lactate in a fluid or tissue in the individual to less than 5 mM. In some embodiments of a subject method, administering the compound or pharmaceutical composition increases the blood pH of the individual by at least 0.02 pH units. In some embodiments of a subject method, administering the compound or pharmaceutical composition increases the blood pH of the individual to a range of from 7.1 to 7.5. A method as provided can further comprise measuring one or both of: (i) the blood lactate level of the individual; and (ii) the blood pH of the individual. In some cases, the boronic acid compound is administered in combination with an anti-cancer agent; the anti-cancer agent can be a cancer chemotherapeutic agent or a cancer immunotherapeutic agent.

The present disclosure provides a method of treating a disease or disorder associated with elevated lactate in an individual, the method comprising administering to the individual an effective amount of:

a) a compound of formula I:

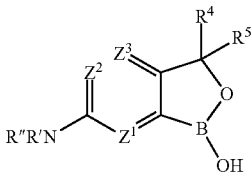

(I)

wherein $Z^1$ is CH, $CR^1$ or N;
$Z^2$ is CH, $CR^2$ or N;
$Z^3$ is CH, $CR^3$ or N;
$R^1$, $R^2$, $R^3$, $R^4$ and $R^5$ are each independently selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO₂-alkyl, —SO₂-substituted alkyl, —SO₂-aryl, —SO₂-heteroaryl and trihalomethyl; and R' and R" are each independently selected from hydrogen, an alkyl, an aryl, substituted alkyl and substituted aryl, and acyl;

b) a compound of formula II:

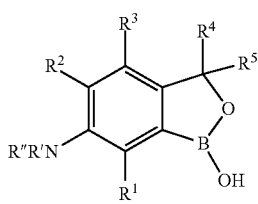

(II)

wherein R¹, R², R³, R⁴ and R⁵ are each independently selected from hydrogen, acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO₂-alkyl, —SO₂-substituted alkyl, —SO₂-aryl, —SO₂-heteroaryl and trihalomethyl; and R' and R" are each independently selected from hydrogen, an alkyl, an aryl, substituted alkyl and substituted aryl, and acyl;

c) a compound of formula III:

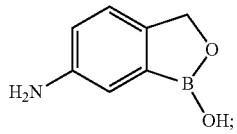

(III)

or d) a pharmaceutical composition comprising a compound of (a), (b), or (c), wherein the compound selectively binds to lactate and reduces the level of lactate in a tissue or fluid in the individual, thereby treating the disease or disorder associated with elevated lactate in the individual. In some cases, the fluid is blood or a blood fraction. In some cases, the disease or disorder associated with elevated lactate levels is lactic acidosis. Other diseases and disorders associated with elevated lactate levels include, e.g., cancer, non-Hodgkin's lymphoma, Burkitt lymphoma, mitochondrial encephalomyopathy, lactic acidosis and stroke-like episodes (MELAS), diabetes mellitus and deafness (DAD), maternally inherited diabetes and deafness (MIDD), glucose-6-phosphatase deficiency, glycogen storage disease type I (GSD I), von Gierke's disease, fructose 1,6-diphosphatase deficiency, pyruvate dehydrogenase deficiency (PDCD), pyruvate carboxylase deficiency, diabetic ketoacidosis, regional hypoperfusion, hepatic disease, shock, sepsis, ethanol toxicity, hemorrhage, hypoxia, hypoperfusion, isoniazid toxicity, phenformin ingestion, metformin ingestion, nucleoside reverse transcriptase inhibitor ingestion, or cyanide ingestion. In some cases, the individual is a mammal. In some instances, the individual is a human. In some cases, an effective amount of the compound is in a range of from 10 μM to 500 mM. In some cases, the boronic acid compound is administered in a total daily dose of from 0.1 mg to 500 mg. In some cases, the compound is administered in a total daily dose of from 0.1 mg to 50 mg. In some embodiments of a subject method, administering the compound or pharmaceutical composition reduces the level of lactate in a fluid or tissue in the individual by at least 5%. In some embodiments of a subject method, administering the compound or pharmaceutical composition reduces the level of lactate in a fluid or tissue in the individual to less than 5 mM. In some embodiments of a subject method, administering the compound or pharmaceutical composition increases the blood pH of the individual by at least 0.02 pH units. In some embodiments of a subject method, administering the compound or pharmaceutical composition increases the blood pH of the individual to a range of from 7.1 to 7.5. The method can further include measuring at least one of: (i) the blood lactate level of the individual; and (ii) the blood pH of the individual. In some embodiments of a subject method, the compound or pharmaceutical composition is administered in combination with an anti-cancer agent; the anti-cancer agent can be a cancer chemotherapeutic agent or a cancer immunotherapeutic agent.

The present disclosure provides a method of treating lactic acidosis in an individual, the method comprising administering to the individual an effective amount of:

a) a compound of formula I:

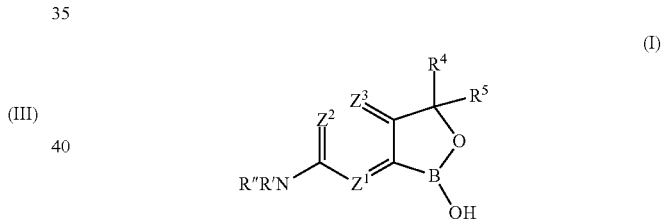

(I)

wherein Z¹ is CH, CR¹ or N;

Z² is CH, CR² or N;

Z³ is CH, CR³ or N;

R¹, R², R³, R⁴ and R⁵ are each independently selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO₂-alkyl, —SO₂-substituted alkyl, —SO₂-aryl, —SO₂-heteroaryl and trihalomethyl; and R' and R" are each independently selected from hydrogen, an alkyl, an aryl, substituted alkyl and substituted aryl, and acyl;

b) a compound of formula II:

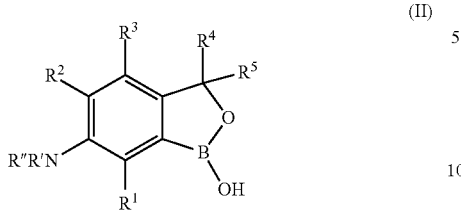

wherein $R^1$, $R^2$, $R^3$, $R^4$ and $R^5$ are each independently selected from hydrogen, acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl; and R' and R" are each independently selected from hydrogen, an alkyl, an aryl, substituted alkyl and substituted aryl, and acyl;

c) a compound of formula III:

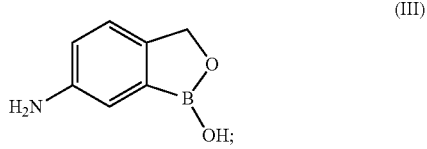 [SMILES: Nc1ccc2c(c1)B(O)OC2]

or d) a pharmaceutical composition comprising a compound of (a), (b), or (c), wherein the boronic acid compound selectively binds to lactate, lowers lactate levels in a body fluid or tissue, and treats the lactic acidosis.

The present disclosure provides a method of treating cancer in an individual, the method comprising administering to the individual an effective amount of an anti-cancer agent and:

a) a compound of formula I:

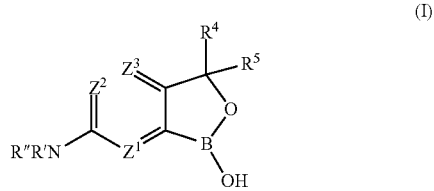

wherein $Z^1$ is CH, $CR^1$ or N;
$Z^2$ is CH, $CR^2$ or N;
$Z^3$ is CH, $CR^3$ or N;
$R^1$, $R^2$, $R^3$, $R^4$ and $R^5$ are each independently selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl; and R' and R" are each independently selected from hydrogen, an alkyl, an aryl, substituted alkyl and substituted aryl, and acyl;

b) a compound of formula II:

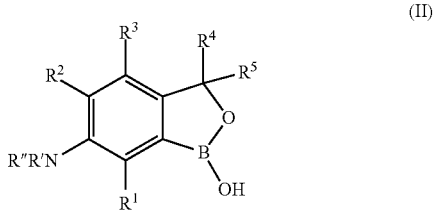

wherein $R^1$, $R^2$, $R^3$, $R^4$ and $R^5$ are each independently selected from hydrogen, acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl; and R' and R" are each independently selected from hydrogen, an alkyl, an aryl, substituted alkyl and substituted aryl, and acyl;

c) a compound of formula III:

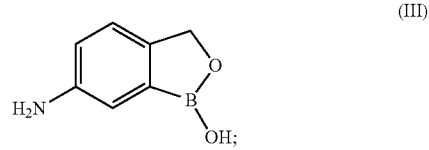

or d) a pharmaceutical composition comprising a compound of (a), (b), or (c), wherein the cancer is a solid tumor, and wherein said administering reduces the size of the solid tumor. In some embodiments, the anti-cancer agent is a cancer chemotherapeutic agent or a cancer immunotherapeutic agent.

DEFINITIONS

Figure 1:
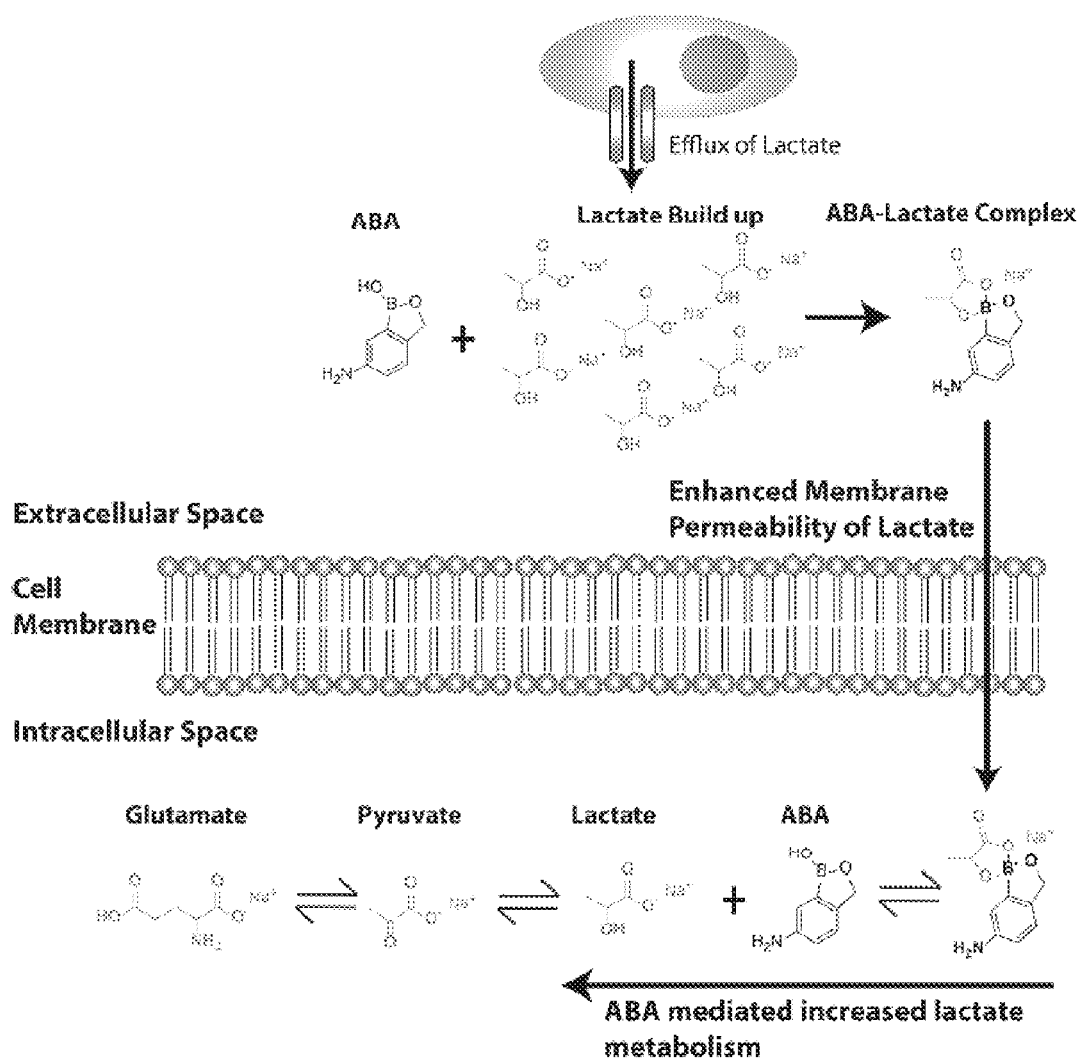
FIG. 1 depicts a schematic depiction of effects of 5-amino-2-hydroxymethylphenyl boronic acid (ABA).

The following terms have the following meanings unless otherwise indicated. Any undefined terms have their art recognized meanings.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—$CH_2$—), ethylene (—$CH_2CH_2$—), n-propylene (—$CH_2CH_2CH_2$—), iso-propylene (—$CH_2CH(CH_3)$—), (—$C(CH_3)_2CH_2CH_2$—), (—C($CH_3)_2CH_2C(O)$—), (—$C(CH_3)_2CH_2C(O)NH$—), (—CH($CH_3)CH_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkenyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—$CH_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O)substituted alkyl, NR$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O)NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O— alkynyl, —O—C(O)O-substituted alkynyl, —O—C(O)O-aryl, —O—C(O)O-substituted aryl, —O—C(O)O—cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cycloalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cycloalkyl, OSO$_2$-cycloalkenyl, OSO$_2$-substituted cycloalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O$^-$)(O)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the present disclosure and the other a typical counter ion such as chloride, or two ionized compounds disclosed herein can serve as counter ions for such divalent alkali earth ions, or a doubly ionized compound of the present disclosure can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S⁻M⁺, —NR⁸⁰R⁸⁰, trihalomethyl, —CF$_3$, —CN, —OCN, —SCN, —NO, —NO$_2$, —N$_3$, —SO$_2$R⁷⁰, —SO$_3$⁻M⁺, —SO$_3$R⁷⁰, —OSO$_2$R⁷⁰, —OSO$_3$⁻M⁺, —OSO$_3$R⁷⁰, —PO$_3$⁻²(M⁺)$_2$, —P(O)(OR⁷⁰)O⁻M⁺, —P(O)(OR⁷⁰)$_2$, —C(O)R⁷⁰, —C(S)R⁷⁰, —C(NR⁷⁰)R⁷⁰, —CO$_2$⁻M⁺, —CO$_2$R⁷⁰, —C(S)OR⁷⁰, —C(O)NR⁸⁰R⁸⁰, —C(NR⁷⁰)NR⁸⁰R⁸⁰, —OC(O)R⁷⁰, —OC(S)R⁷⁰, —OCO$_2$⁻M⁺, —OCO$_2$R⁷⁰, —OC(S)OR⁷⁰, —NR⁷⁰C(O)R⁷⁰, —NR⁷⁰C(S)R⁷⁰, —NR⁷⁰CO$_2$⁻M⁺, —NR⁷⁰CO$_2$R⁷⁰, —NR⁷⁰C(S)OR⁷⁰, —NR⁷⁰C(O)NR⁸⁰R⁸⁰, —NR⁷⁰C(NR⁷⁰)R⁷⁰ and —NR⁷⁰C(NR⁷⁰)NR⁸⁰R⁸⁰, where R⁶⁰, R⁷⁰, R⁸⁰ and M⁺ are as previously defined, provided that in case of substituted alkene or alkyne, the substituents are not —O⁻M⁺, —OR⁷⁰, —SR⁷⁰, or —S⁻M⁺.

In addition to the groups disclosed with respect to the individual terms herein, substituent groups for hydrogens on nitrogen atoms in "substituted" heteroalkyl and cycloheteroalkyl groups are, unless otherwise specified, —R⁶⁰, —O⁻M⁺, —OR⁷⁰, —SR⁷⁰, —S⁻M⁺, —NR⁸⁰R⁸⁰, trihalomethyl, —CF$_3$, —CN, —NO, —NO$_2$, —S(O)$_2$R⁷⁰, —S(O)$_2$O⁻M⁺, —S(O)$_2$OR⁷⁰, —OS(O)$_2$R⁷⁰, —OS(O)$_2$OR⁷⁰, —P(O)(O⁻)$_2$(M⁺)$_2$, —P(O)(OR⁷⁰)O⁻M⁺, —P(O)(OR⁷⁰)(OR⁷⁰), —C(O)R⁷⁰, —C(S)R⁷⁰, —C(NR⁷⁰)R⁷⁰, —C(O)OR⁷⁰, —C(S)OR⁷⁰, —C(O)NR⁸⁰R⁸⁰, —C(NR⁷⁰)NR⁸⁰R⁸⁰, —OC(O)R⁷⁰, —OC(S)R⁷⁰, —OC(O)OR⁷⁰, —OC(S)OR⁷⁰, —NR⁷⁰C(O)R⁷⁰, —NR⁷⁰C(S)R⁷⁰, —NR⁷⁰C(O)OR⁷⁰, —NR⁷⁰C(S)OR⁷⁰, —NR⁷⁰C(O)NR⁸⁰R⁸⁰, —NR⁷⁰C(NR⁷⁰)R⁷⁰ and —NR⁷⁰C(NR⁷⁰)NR⁸⁰R⁸⁰, where R⁶⁰, R⁷⁰, R⁸⁰ and M⁺ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautomeric ring atom arrangements are possible.

The terms "treatment", "treating", "treat" and the like are used herein to generally refer to obtaining a desired pharmacologic and/or physiologic effect. The effect can be prophylactic in terms of completely or partially preventing a disease, condition, or symptom(s) thereof and/or may be therapeutic in terms of a partial or complete stabilization or cure for a disease or condition, and/or adverse effect attributable to the disease or condition. The term "treatment" encompasses any treatment of a disease or condition in a mammal, particularly a human, and includes: (a) preventing the disease, condition, and/or symptom(s) from occurring in a subject who may be predisposed to the disease, condition, and/or symptom(s) but has not yet been diagnosed as having it; (b) inhibiting the disease, condition, and/or symptom(s), i.e., arresting development of a disease, condition, and/or the associated symptoms; or (c) relieving the disease, condition, and/or the associated symptom(s), i.e., causing regression of the disease, condition, and/or symptom(s). Those in need of treatment can include those already inflicted (e.g., those with elevated lactate levels) as well as those in which prevention is desired.

The terms "recipient", "individual", "subject", "host", and "patient", are used interchangeably herein and refer to any mammalian subject for whom diagnosis, treatment, or therapy is desired, e.g., a human. "Mammal" for purposes of treatment refers to any animal classified as a mammal, including humans, domestic and farm animals, laboratory animals such as rodents, and zoo, sports, or pet animals, such as dogs, horses, cats, cows, sheep, goats, pigs, camels, etc. In some embodiments, the mammal is human. In some embodiments, the mammal is a rodent, e.g., a rat or a mouse. In some embodiments, the mammal is a non-human primate.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a boronic acid compound" includes a plurality of such compounds and reference to "the pharmaceutical composition" includes reference to one or more pharmaceutical compositions and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods of reducing levels of lactate in a fluid or tissue in an individual. The present disclosure provides pharmaceutical compositions suitable for use in the methods.

Methods of Reducing Lactate Levels

The present disclosure provides a method of reducing the level of lactate in a fluid or tissue of an individual. The method generally involves administering to the individual an effective amount of a boronic acid compound, or a pharmaceutical composition comprising such a compound, to the individual.

In some embodiments, an effective amount of a boronic acid compound is one that reduces the level of lactate in a fluid or tissue of an individual by at least about 5%, at least about 10%, at least about 15%, at least about 20%, at least about 25%, at least about 30%, at least about 40%, at least about 50%, at least about 60%, at least about 70%, or more than 70%, compared to the level of lactate in the fluid or tissue before treatment with the boronic acid compound.

In some embodiments, an effective amount of a boronic acid compound is one that reduces the level of lactate in a fluid or tissue of an individual to within a normal range, e.g., to about 2 mM.

In some embodiments, an effective amount of a boronic acid compound is one that reduces the level of lactate in a fluid or tissue of an individual to less than about 5 mM, e.g., to from about 5 mM to about 3 mM, from about 3 mM to about 2 mM, from about 2 mM to about 1 mM, or from about 1 mM to about 0.5 mM.

In some embodiments, an effective amount of a boronic acid compound is one that increases the pH of a body fluid (e.g., blood) by at least about 0.02 pH units. In some embodiments, an effective amount of a boronic acid compound is one that increases the pH of a body fluid (e.g., blood) to within a normal range, e.g., to within pH 7.1-7.5.

Fluids include any body fluid, where body fluids include, but are not limited to, blood; a blood product (serum; plasma); cerebrospinal fluid; bronchoalveolar lavage fluid; interstitial fluid; saliva; urine; intracellular fluid; and the like. In some cases, the fluid is an extracellular fluid.

Tissues include any tissue of the body, including, e.g., pathological tissues such as a solid tumor; an organ; and the like.

Boronic Acid Compounds

Boronic acid compounds suitable for use in a subject method include, but are not limited to, an aryl- or heteroaryl-boronic acid compound substituted at the 2-position with a hydroxyalkyl group, where the hydroxyalkyl group may be further substituted with any convenient alkyl substitutent. In some cases, the hydroxyalkyl group is a 2-hydroxymethyl group. The aryl- or heteroaryl-boronic acid compounds may be further substituted with one or more substitutents at any convenient position, such as a substituted or unsubstituted amino group. In certain instances, the compound includes an amino group at the 5-position of the aryl or heteryl-boronic acid compound, where the amino group may be substituted or unsubstituted.

In some embodiments, the compound is described by formula I:

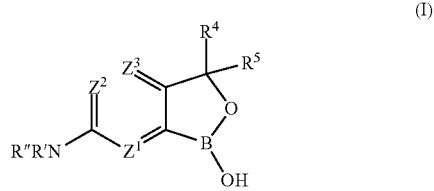

wherein:

$Z^1$ is CH, $CR^1$ or N;
$Z^2$ is CH, $CR^2$ or N;
$Z^3$ is CH, $CR^3$ or N;

$R^1$, $R^2$, $R^3$, $R^4$ and $R^5$ are each independently selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl;

R' and R" are each independently selected from hydrogen, an alkyl, an aryl, substituted alkyl and substituted aryl, and acyl.

In certain embodiments, in formula I, $R^4$ and $R^5$ are each hydrogen.

In certain embodiments, in formula I, R' and R" are each hydrogen.

In certain embodiments, in formula I, $Z^1$, $Z^2$ and $Z^3$ are each CH.

In some embodiments, the compound is described by formula II:

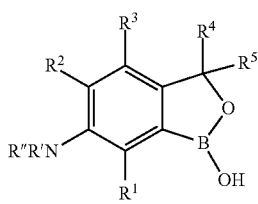

(II)

wherein $R^1$, $R^2$, $R^3$, $R^4$ and $R^5$ are each independently selected from hydrogen, acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl; and R' and R" are each independently selected from hydrogen, an alkyl, an aryl, substituted alkyl and substituted aryl, and acyl.

In certain embodiments, in formula I, $R^1$, $R^2$ and $R^3$, are each hydrogen.

In certain embodiments, in formula I, $R^4$ and $R^5$ are each hydrogen.

In certain embodiments, in formula I, R' and R" are each hydrogen.

In some embodiments, the compound is described by formula III:

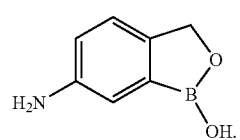

(III)

Any one of the boronic acid compounds described herein may also be represented by a structure that includes a 2-hydroxymethyl group that is not bonded to the boron atom, as represented as follows for formula (III):

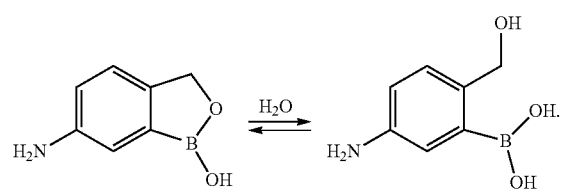

Treatment Methods

The present disclosure provides methods of treating a disease or disorder in an individual, where the disease or disorder is associated with elevated lactate levels in a fluid or tissue in the individual. The method generally involves administering to an individual in need thereof an effective amount of a boronic acid compound, as described above, or a pharmaceutical composition comprising the boronic acid compound.

For example, a subject treatment method can comprise administering to an individual in need thereof an effective amount of:

a) a compound of formula I:

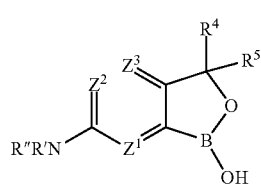

(I)

wherein $Z^1$ is CH, $CR^1$ or N;
$Z^2$ is CH, $CR^2$ or N;
$Z^3$ is CH, $CR^3$ or N;

$R^1$, $R^2$, $R^3$, $R^4$ and $R^5$ are each independently selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl; and R' and R" are each independently selected from hydrogen, an alkyl, an aryl, substituted alkyl and substituted aryl, and acyl;

b) a compound of formula II:

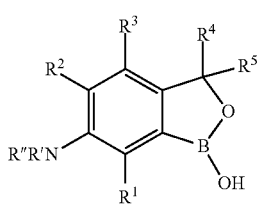

wherein $R^1$, $R^2$, $R^3$, $R^4$ and $R^5$ are each independently selected from hydrogen, acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO—alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl; and R' and R" are each independently selected from hydrogen, an alkyl, an aryl, substituted alkyl and substituted aryl, and acyl;

c) a compound of formula III:

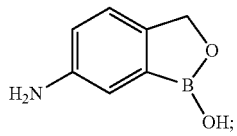

or d) a pharmaceutical composition comprising a compound of (a), (b), or (c).

In some embodiments, an effective amount of a boronic acid compound is one that reduces the level of lactate in a fluid or tissue of an individual by at least about 5%, at least about 10%, at least about 15%, at least about 20%, at least about 25%, at least about 30%, at least about 40%, at least about 50%, at least about 60%, at least about 70%, or more than 70%, compared to the level of lactate in the fluid or tissue before treatment with the boronic acid compound.

In some embodiments, an effective amount of a boronic acid compound is one that reduces the level of lactate in a fluid or tissue of an individual to within a normal range.

In some embodiments, an effective amount of a boronic acid compound is one that reduces the level of lactate in a fluid or tissue of an individual to less than about 5 mM, e.g., to from about 5 mM to about 3 mM, from about 3 mM to about 2 mM, from about 2 mM to about 1 mM, or from about 1 mM to about 0.5 mM.

Diseases and disorders associated with elevated lactate levels include, e.g., cancer, non-Hodgkin's lymphoma, Burkitt lymphoma, mitochondrial encephalomyopathy, lactic acidosis and stroke-like episodes (MELAS), diabetes mellitus and deafness (DAD), maternally inherited diabetes and deafness (MIDD), glucose-6-phosphatase deficiency, glycogen storage disease type I (GSD I), von Gierke's disease, fructose 1,6-diphosphatase deficiency, pyruvate dehydrogenase deficiency (PDCD), pyruvate carboxylase deficiency, diabetic ketoacidosis, regional hypoperfusion, hepatic disease, shock, sepsis, ethanol toxicity, hemorrhage, hypoxia, hypoperfusion, isoniazid toxicity, phenformin ingestion, metformin ingestion, nucleoside reverse transcriptase inhibitor ingestion, cyanide ingestion, liver failure, kidney failure or diseases causing liver or kidney failure, and sports or exercise-related lactic acidosis.

Lactic Acidosis

The present disclosure provides a method for treating lactic acidosis in an individual, the method generally administering to an individual in need thereof an effective amount of a boronic acid compound, as described above, or a pharmaceutical composition comprising the boronic acid compound.

For example, a subject treatment method can comprise administering to an individual in need thereof an effective amount of:

a) a compound of formula I:

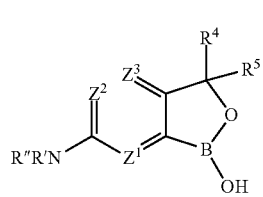

wherein $Z^1$ is CH, $CR^1$ or N;
$Z^2$ is CH, $CR^2$ or N;
$Z^3$ is CH, $CR^3$ or N;
$R^1$, $R^2$, $R^3$, $R^4$ and $R^5$ are each independently selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl; and R' and R" are each independently selected from hydrogen, an alkyl, an aryl, substituted alkyl and substituted aryl, and acyl;

b) a compound of formula II:

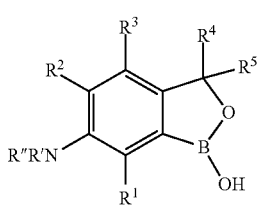

wherein $R^1$, $R^2$, $R^3$, $R^4$ and $R^5$ are each independently selected from hydrogen, acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO—alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl; and R' and R" are each independently selected from hydrogen, an alkyl, an aryl, substituted alkyl and substituted aryl, and acyl;

c) a compound of formula III:

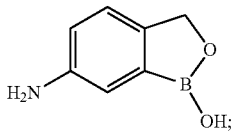

or d) a pharmaceutical composition comprising a compound of (a), (b), or (c).

In some embodiments, an effective amount of a boronic acid compound is one that reduces the level of lactate in a fluid or tissue of an individual by at least about 5%, at least about 10%, at least about 15%, at least about 20%, at least about 25%, at least about 30%, at least about 40%, at least about 50%, at least about 60%, at least about 70%, or more than 70%, compared to the level of lactate in the fluid or tissue before treatment with the boronic acid compound.

In some embodiments, an effective amount of a boronic acid compound is one that reduces the level of lactate in a fluid or tissue of an individual to within a normal range.

In some embodiments, an effective amount of a boronic acid compound is one that reduces the level of lactate in a fluid or tissue of an individual to less than about 5 mM, e.g., to from about 5 mM to about 3 mM, from about 3 mM to about 2 mM, from about 2 mM to about 1 mM, or from about 1 mM to about 0.5 mM.

Cancer Treatment

The present disclosure provides a method of treating cancer in an individual, the method generally involving administering to an individual in need thereof an effective amount of: 1) a boronic acid compound, as described above, or a pharmaceutical composition comprising the boronic acid compound; and 2) an anti-cancer agent.

For example, a subject treatment method can comprise administering to an individual in need thereof an effective amount of an anti-cancer agent and:

a) a compound of formula I:

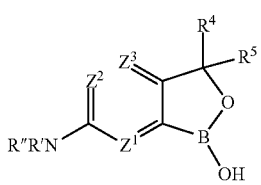

wherein $Z^1$ is CH, $CR^1$ or N;
$Z^2$ is CH, $CR^2$ or N;
$Z^3$ is CH, $CR^3$ or N;

$R^1$, $R^2$, $R^3$, $R^4$ and $R^5$ are each independently selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl; and R' and R" are each independently selected from hydrogen, an alkyl, an aryl, substituted alkyl and substituted aryl, and acyl;

b) a compound of formula II:

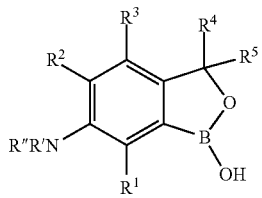

wherein $R^1$, $R^2$, $R^3$, $R^4$ and $R^5$ are each independently selected from hydrogen, acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO—alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl; and R' and R" are each independently selected from hydrogen, an alkyl, an aryl, substituted alkyl and substituted aryl, and acyl;

c) a compound of formula III:

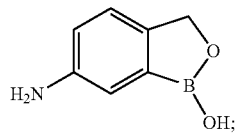

or d) a pharmaceutical composition comprising a compound of (a), (b), or (c).

In some embodiments, an effective amount of a boronic acid compound is one that reduces the level of lactate in a fluid or tissue of an individual by at least about 5%, at least about 10%, at least about 15%, at least about 20%, at least about 25%, at least about 30%, at least about 40%, at least about 50%, at least about 60%, at least about 70%, or more than 70%, compared to the level of lactate in the fluid or tissue before treatment with the boronic acid compound.

In some embodiments, an effective amount of a boronic acid compound is one induces apoptosis in a cancer cell in the individual.

In some embodiments, an effective amount of a boronic acid compound is one that reduces the size of a solid tumor in the individual by at least about 5%, at least about 10%, at least about 20%, at least about 25%, at least about 30%, at least about 40%, at least about 50%, at least about 60%, at least about 70%, or more than 70%, compared to the size of the tumor in the absence of treatment with the boronic compound and the anti-cancer agent.

An anti-cancer agent suitable for use in a subject method can be a cancer chemotherapeutic agent and/or a cancer immunotherapeutic agent.

A subject method for treating cancer can also include radiation therapy. Radiation therapy includes, but is not limited to, x-rays or gamma rays that are delivered from either an externally applied source such as a beam, or by implantation of small radioactive sources. For example, radiation therapy includes external beam radiation therapy and brachytherapy.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation; therefore, compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3N-desbenzoyl-3N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers suitable for use in connection with the methods of the present disclosure for treating cancer include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-γ; (8) colony-stimulating factors; (9) inhibitors of angiogenesis; and (10) antagonists of tumor necrosis factor.

Cancer immunotherapeutic agents include antibodies specific for a tumor antigen. Non-limiting examples include, e.g., an anti-HER-2 antibody such as Herceptin®; an anti-CD20 antibody such as Rituxan®; an anti-CD52 antibody such as MabCampath®; an anti-vascular endothelial growth factor (VEGF) antibody such as Avastin®; an anti-CD47 antibody; an anti-epidermal growth factor receptor antibody such as Cetuximab®; and the like.

Pharmaceutical Compositions, Dosages, Routes of Administration

An active agent (e.g., boronic compound) can be provided together with a pharmaceutically acceptable excipient. Pharmaceutically acceptable excipients are known to those skilled in the art, and have been amply described in a variety of publications, including, for example, A. Gennaro (1995) "Remington: The Science and Practice of Pharmacy", 19th edition, Lippincott, Williams, & Wilkins. In the discussion, below, of formulations, dosages, and routes of delivery, an "active agent" will refer to a boronic compound as described above and/or at least a second therapeutic agent, unless otherwise specified.

An active agent (e.g., a boronic acid compound as described above) can be incorporated into a variety of formulations for therapeutic administration. More particularly, an active agent can be formulated into pharmaceutical compositions by combination with appropriate pharmaceutically acceptable carriers or diluents, and may be formulated into preparations in solid, semi-solid, liquid or gaseous forms, such as, powders, granules, solutions, injections, inhalants, gels, hydrogels, microspheres, etc. As such, administration of an active agent can be achieved in various ways, including local, such as delivery into the affected tissue, oral, catheter mediated, intrathecal, buccal, parenteral, intraperitoneal, intradermal, transdermal, intratracheal, etc., administration. The active agent may be systemic after administration or may be localized by the use of regional administration, intramural administration, or use of an implant that acts to retain the active dose at the site of implantation.

In some embodiments, an active agent(s) is formulated to cross the blood brain barrier (BBB). One strategy for drug delivery through the blood brain barrier (BBB) entails disruption of the BBB, either by osmotic means such as mannitol or leukotrienes, or biochemically by the use of vasoactive substances such as brakykinin. A BBB disrupting agent can be co-administered with an active agent when the compositions are administered by intravascular injection. Other strategies to go through the BBB may entail the use of endogenous transport systems, including carrier-mediated transporters such as glucose and amino acid carriers, receptor-mediated transcytosis for insulin or transferrin, and active efflux transporters such as p-glycoprotein. Active transport moieties may also be conjugated to an active agent for use in the methods disclosed herein to facilitate transport across the epithelial wall of the blood vessel. Alternatively, drug delivery behind the BBB is by intrathecal delivery of therapeutics directly to the cranium, as through an Ommaya reservoir.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, phosphate buffered saline (PBS), Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see. Langer, Science 249: 1527-1533 (1990).

The pharmaceutical compositions can be administered for prophylactic and/or therapeutic treatments. Toxicity and therapeutic efficacy of the active agent can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred.

The data obtained from cell culture and/or animal studies can be used in formulating a range of dosages for humans. The dosage of the active agent typically lines within a range of circulating concentrations that include the ED50 with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under Good Manufacturing Practice (GMP) conditions.

The effective amount of an active agent(s) to be given to a particular patient will depend on a variety of factors, several of which will be different from patient to patient. A competent clinician will be able to determine an effective amount of an active agent to administer to a patient to treat a given disorder. Utilizing LD50 animal data, and other information available for the inhibitor, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

Formulations

In carrying out a subject treatment method, an active agent(s) (e.g., a boronic acid compound) can be administered to the host using any convenient means capable of resulting in the desired physiological effect (e.g., decrease in lactate levels). Thus, an active agent (e.g., a boronic acid compound) can be incorporated into a variety of formulations for therapeutic administration. More particularly, an active agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, an active agent(s) can be administered in the form of its (their) pharmaceutically acceptable salts, or the active agent may also be used alone or in appropriate association, as well as in combination, with other pharmaceutically active compounds. The following methods and excipients are merely exemplary and are in no way limiting.

For oral preparations, an active agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An active agent can be formulated into preparations for injection by dissolving, suspending or emulsifying the active agent in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

An active agent can be utilized in aerosol formulation to be administered via inhalation. The compounds of the present disclosure can be formulated into pressurized acceptable propellants such as dichlorodifluoromethane, propane, nitrogen and the like.

Furthermore, an active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more active agents. Similarly, unit dosage forms for injection or intravenous administration may comprise the active agent(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of an active agent calculated in an amount sufficient to produce the desired effect in association with a pharmaceutically acceptable diluent, carrier or vehicle. The specifications for a unit dosage form of an active agent depend on the particular active agent employed and the effect to be achieved, and the pharmacodynamics associated with each active agent in the host.

Other modes of administration will also find use. For instance, an active agent can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), e.g., about 1% to about 2%.

Intranasal formulations will usually include vehicles that neither cause irritation to the nasal mucosa nor significantly disturb ciliary function. Diluents such as water, aqueous saline or other known substances can be employed. The nasal formulations may also contain preservatives such as, but not limited to, chlorobutanol and benzalkonium chloride. A surfactant may be present to enhance absorption of an active agent by the nasal mucosa.

An active agent can be administered in an injectable form, e.g., the active agent can be in a formulation suitable for injection (e.g., intravenous injection, intramuscular injection, subcutaneous injection, intrathecal injection, etc.). Injectable compositions can be prepared as liquid solutions or suspensions; solid forms suitable for solution in, or suspension in, liquid vehicles prior to injection may also be prepared. The preparation may also be emulsified or the active agent encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the active agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Oral Formulations

In some embodiments, an active agent (e.g., a boronic acid compound) is formulated for oral delivery to an individual in need of such an agent.

For oral delivery, a formulation comprising an active agent will in some embodiments include an enteric-soluble coating material. Suitable enteric-soluble coating material include hydroxypropyl methylcellulose acetate succinate (HPMCAS), hydroxypropyl methyl cellulose phthalate (HP- MCP), cellulose acetate phthalate (CAP), polyvinyl phthalic acetate (PVPA), Eudragit™, and shellac.

As one non-limiting example of a suitable oral formulation, an active agent is formulated with one or more pharmaceutical excipients and coated with an enteric coating, as described in U.S. Pat. No. 6,346,269. For example, a solution comprising an active agent and a stabilizer is coated onto a core comprising pharmaceutically acceptable excipients, to form an active agent-coated core; a sub-coating layer is applied to the active agent-coated core, which is then coated with an enteric coating layer. The core generally includes pharmaceutically inactive components such as lactose, a starch, mannitol, sodium carboxymethyl cellulose, sodium starch glycolate, sodium chloride, potassium chloride, pigments, salts of alginic acid, talc, titanium dioxide, stearic acid, stearate, micro-crystalline cellulose, glycerin, polyethylene glycol, triethyl citrate, tributyl citrate, propanyl triacetate, dibasic calcium phosphate, tribasic sodium phosphate, calcium sulfate, cyclodextrin, and castor oil. Suitable solvents for an active agent include aqueous solvents. Suitable stabilizers include alkali-metals and alkaline earth metals, bases of phosphates and organic acid salts and organic amines. The sub-coating layer comprises one or more of an adhesive, a plasticizer, and an anti-tackiness agent. Suitable anti-tackiness agents include talc, stearic acid, stearate, sodium stearyl fumarate, glyceryl behenate, kaolin and aerosil. Suitable adhesives include polyvinyl pyrrolidone (PVP), gelatin, hydroxyethyl cellulose (HEC), hydroxypropyl cellulose (HPC), hydroxypropyl methyl cellulose (HPMC), vinyl acetate (VA), polyvinyl alcohol (PVA), methyl cellulose (MC), ethyl cellulose (EC), hydroxypropyl methyl cellulose phthalate (HPMCP), cellulose acetate phthalates (CAP), xanthan gum, alginic acid, salts of alginic acid, Eudragit™, copolymer of methyl acrylic acid/methyl methacrylate with polyvinyl acetate phthalate (PVAP). Suitable plasticizers include glycerin, polyethylene glycol, triethyl citrate, tributyl citrate, propanyl triacetate and castor oil. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™ and shellac.

Suitable oral formulations also include an active agent, formulated with any of the following: microgranules (see, e.g., U.S. Pat. No. 6,458,398); biodegradable macromers (see, e.g., U.S. Pat. No. 6,703,037); biodegradable hydrogels (see, e.g., Graham and McNeill (1989) *Biomaterials* 5:27-36); biodegradable particulate vectors (see, e.g., U.S. Pat. No. 5,736,371); bioabsorbable lactone polymers (see, e.g., U.S. Pat. No. 5,631,015); slow release protein polymers (see, e.g., U.S. Pat. No. 6,699,504; Pelias Technologies, Inc.); a poly(lactide-co-glycolide/polyethylene glycol block copolymer (see, e.g., U.S. Pat. No. 6,630,155; Atrix Laboratories, Inc.); a composition comprising a biocompatible polymer and particles of metal cation-stabilized agent dispersed within the polymer (see, e.g., U.S. Pat. No. 6,379,701; Alkermes Controlled Therapeutics, Inc.); and microspheres (see, e.g., U.S. Pat. No. 6,303,148; Octoplus, B.V.).

Suitable oral formulations also include an active agent formulated with any of the following: a carrier such as Emisphere® (Emisphere Technologies, Inc.); TIMERx, a hydrophilic matrix combining xanthan and locust bean gums which, in the presence of dextrose, form a strong binder gel in water (Penwest); Geminex™ (Penwest); Procise™ (GlaxoSmithKline); SAVIT™ (Mistral Pharma Inc.); Ring-Cap™ (Alza Corp.); Smartrix® (Smartrix Technologies, Inc.); SQZgel™ (MacroMed, Inc.); Geomatrix™ (Skye Pharma, Inc.); Oros® Tri-layer (Alza Corporation); and the like.

Also suitable for use are formulations such as those described in U.S. Pat. No. 6,296,842 (Alkermes Controlled Therapeutics, Inc.); U.S. Pat. No. 6,187,330 (Scios, Inc.); and the like.

Also suitable for use herein are formulations comprising an intestinal absorption enhancing agent. Suitable intestinal absorption enhancers include, but are not limited to, calcium chelators (e.g., citrate, ethylenediamine tetracetic acid); surfactants (e.g., sodium dodecyl sulfate, bile salts, palmitoylcarnitine, and sodium salts of fatty acids); toxins (e.g., zonula occludens toxin); and the like.

Controlled Release Formulations

In some embodiments, an active agent is formulated in a controlled release formulation.

Controlled release formulations suitable for use can be taken to mean any one of a number of extended release dosage forms. The following terms may be considered to be substantially equivalent to controlled release, for the purposes of the present disclosure: continuous release, controlled release, delayed release, depot, gradual release, long-term release, programmed release, prolonged release, proportionate release, protracted release, repository, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, *Extended-Release Dosage Forms*, 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable); and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, *Controlled Release Technologies: Methods, Theory and Applications*, 1980 (CRC Press, Inc.).

There are a number of controlled release drug formulations that are developed for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems may be found in Yie W. Chien, *Novel Drug Delivery Systems*, 1992 (Marcel Dekker, Inc.). Some of these formulations will now be discussed in more detail.

Enteric coatings are applied to tablets to prevent the release of drugs in the stomach either to reduce the risk of unpleasant side effects or to maintain the stability of the drug which might otherwise be subject to degradation of expose to the gastric environment. Polymers that are used for this purpose include polyacids that function by virtue or the fact that their solubility in aqueous medium is pH-dependent, and they require conditions with a pH higher than normally encountered in the stomach.

One exemplary type of oral controlled release structure is enteric coating of a solid or liquid dosage form. The enteric coatings are designed to disintegrate in intestinal fluid for ready absorption. Delay of absorption of the active agent that is incorporated into a formulation with an enteric coating is dependent on the rate of transfer through the gastrointestinal tract, and so the rate of gastric emptying is an important factor. Some investigators have reported that a multiple-unit type dosage form, such as granules, may be superior to a single-unit type. Therefore, in one exemplary embodiment, an active agent may be contained in an enterically coated multiple-unit dosage form. In an exemplary embodiment, an active agent dosage form is prepared by spray-coating granules of an active agent-enteric coating agent solid dispersion on an inert core material. These granules can result in prolonged absorption of the drug with good bioavailability.

Suitable enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa, *Application of solid dispersions of Nifedipine with enteric coating agent to prepare a sustained-release dosage form*, Chem. Pharm. Bull. 33: 1615-1619 (1985). Various enteric coating materials may be selected on the basis of testing to achieve an enteric coated dosage form designed ab initio to have an optimal combination of dissolution time, coating thicknesses and diametral crushing strength. S. C. Porter et al., *The Properties of Enteric Tablet Coatings Made From Polyvinyl Acetate-phthalate and Cellulose acetate Phthalate*, J. Pharm. Pharmacol. 22:42 p (1970).

Another type of useful oral controlled release structure is a solid dispersion. A solid dispersion may be defined as a dispersion of one or more active ingredients in an inert carrier or matrix in the solid state prepared by the melting (fusion), solvent, or melting-solvent method. Akihiko Hasegawa, *Super Saturation Mechanism of Drugs from Solid Dispersions with Enteric Coating Agents*, Chem. Pharm. Bull. 36: 4941-4950 (1998). The solid dispersions may be also called solid-state dispersions. The term "coprecipitates" may also be used to refer to those preparations obtained by the solvent methods.

The selection of the carrier may have an influence on the dissolution characteristics of the dispersed active agent because the dissolution rate of a component from a surface may be affected by other components in a multiple component mixture. For example, a water-soluble carrier may result in a fast release of the active agent from the matrix, or a poorly soluble or insoluble carrier may lead to a slower release of the active agent from the matrix. The solubility of the active agent may also be increased owing to some interaction with the carriers.

Examples of carriers useful in solid dispersions include, but are not limited to, water-soluble polymers such as polyethylene glycol, polyvinylpyrrolidone, and hydroxypropylmethylcellulose. Alternative carriers include phosphatidylcholine. Phosphatidylcholine is an amphoteric but water-insoluble lipid, which may improve the solubility of otherwise insoluble active agents in an amorphous state in phosphatidylcholine solid dispersions.

Other carriers include polyoxyethylene hydrogenated castor oil. Poorly water-soluble active agents may be included in a solid dispersion system with an enteric polymer such as hydroxypropylmethylcellulose phthalate and carboxymethylethylcellulose, and a non-enteric polymer, hydroxypropylmethylcellulose. Another solid dispersion dosage form includes incorporation of the active agent with ethyl cellulose and stearic acid in different ratios.

There are various methods commonly known for preparing solid dispersions. These include, but are not limited to, the melting method, the solvent method and the melting-solvent method.

Another controlled release dosage form is a complex between an ion exchange resin and an active agent. Ion exchange resin-drug complexes have been used to formulate sustained-release products of acidic and basic drugs. In one exemplary embodiment, a polymeric film coating is provided to the ion exchange resin-drug complex particles, making drug release from these particles diffusion controlled. See Y. Raghunathan et al., *Sustained-released drug delivery system I: Coded ion-exchange resin systems for phenylpropanolamine and other drugs*, J. Pharm. Sciences 70: 379-384 (1981).

Injectable microspheres are another controlled release dosage form. Injectable micro spheres may be prepared by non-aqueous phase separation techniques, and spray-drying techniques. Microspheres may be prepared using polylactic acid or copoly(lactic/glycolic acid). Shigeyuki Takada, *Utilization of an Amorphous Form of a Water-Soluble GPIIb/IIIa Antagonist for Controlled Release From Biodegradable Micro spheres*, Pharm. Res. 14:1146-1150 (1997), and ethyl cellulose, Yoshiyuki Koida, *Studies on Dissolution Mechanism of Drugs from Ethyl Cellulose Microcapsules*, Chem. Pharm. Bull. 35:1538-1545 (1987).

Other controlled release technologies that may be used include, but are not limited to, SODAS (Spheroidal Oral Drug Absorption System), INDAS (Insoluble Drug Absorption System), IPDAS (Intestinal Protective Drug Absorption System), MODAS (Multiporous Oral Drug Absorption System), EFVAS (Effervescent Drug Absorption System), PRODAS (Programmable Oral Drug Absorption System), and DUREDAS (Dual Release Drug Absorption System) available from Elan Pharmaceutical Technologies. SODAS are multi particulate dosage forms utilizing controlled release beads. INDAS are a family of drug delivery technologies designed to increase the solubility of poorly soluble drugs. IPDAS are multi particulate tablet formation utilizing a combination of high density controlled release beads and an immediate release granulate. MODAS are controlled release single unit dosage forms. Each tablet consists of an inner core surrounded by a semipermeable multiparous membrane that controls the rate of drug release. EFVAS is an effervescent drug absorption system. PRODAS is a family of multi particulate formulations utilizing combinations of immediate release and controlled release mini-tablets. DUREDAS is a bilayer tablet formulation providing dual release rates within the one dosage form. Although these dosage forms are known to one of skill, certain of these dosage forms will now be discussed in more detail.

INDAS was developed specifically to improve the solubility and absorption characteristics of poorly water soluble drugs. Solubility and, in particular, dissolution within the fluids of the gastrointestinal tract is a key factor in determining the overall oral bioavailability of poorly water soluble drug. By enhancing solubility, one can increase the overall bioavailability of a drug with resulting reductions in dosage.

IPDAS is a multi-particulate tablet technology that may enhance the gastrointestinal tolerability of potential irritant and ulcerogenic drugs. Intestinal protection is facilitated by the multi-particulate nature of the IPDAS formulation which promotes dispersion of an irritant lipoate throughout the gastrointestinal tract. Controlled release characteristics of the individual beads may avoid high concentration of active agent being both released locally and absorbed systemically. The combination of both approaches serves to minimize the potential harm of the active agent with resultant benefits to patients.

IPDAS is composed of numerous high density controlled release beads. Each bead may be manufactured by a two step process that involves the initial production of a micromatrix with embedded active agent and the subsequent coating of this micromatrix with polymer solutions that form a rate-limiting semipermeable membrane in vivo. Once an IPDAS tablet is ingested, it may disintegrate and liberate the beads in the stomach. These beads may subsequently pass into the duodenum and along the gastrointestinal tract, e.g., in a controlled and gradual manner, independent of the feeding state. Release of the active agent occurs by diffusion process through the micromatrix and subsequently through the pores in the rate controlling semipermeable membrane. The release rate from the IPDAS tablet may be customized to deliver a drug-specific absorption profile associated with optimized clinical benefit. Should a fast onset of activity be necessary, immediate-release granulate may be included in the tablet. The tablet may be broken prior to administration, without substantially compromising drug release, if a reduced dose is required for individual titration.

MODAS is a drug delivery system that may be used to control the absorption of water soluble agents. Physically MODAS is a non-disintegrating table formulation that manipulates drug release by a process of rate limiting diffusion by a semipermeable membrane formed in vivo. The diffusion process essentially dictates the rate of presentation of drug to the gastrointestinal fluids, such that the uptake into the body is controlled. Because of the minimal use of excipients, MODAS can readily accommodate small dosage size forms. Each MODAS tablet begins as a core containing active drug plus excipients. This core is coated with a solution of insoluble polymers and soluble excipients. Once the tablet is ingested, the fluid of the gastrointestinal tract may dissolve the soluble excipients in the outer coating leaving substantially the insoluble polymer. What results is a network of tiny, narrow channels connecting fluid from the gastrointestinal tract to the inner drug core of water soluble drug. This fluid passes through these channels, into the core, dissolving the drug, and the resultant solution of drug may diffuse out in a controlled manner. This may permit both controlled dissolution and absorption. An advantage of this system is that the drug releasing pores of the tablet are distributed over substantially the entire surface of the tablet. This facilitates uniform drug absorption reduces aggressive unidirectional drug delivery. MODAS represents a very flexible dosage form in that both the inner core and the outer semipermeable membrane may be altered to suit the individual delivery requirements of a drug. In particular, the addition of excipients to the inner core may help to produce a microenvironment within the tablet that facilitates more predictable release and absorption rates. The addition of an immediate release outer coating may allow for development of combination products.

Additionally, PRODAS may be used to deliver an active agent. PRODAS is a multi particulate drug delivery technology based on the production of controlled release mini tablets in the size range of 1.5 to 4 mm in diameter. The PRODAS technology is a hybrid of multi particulate and hydrophilic matrix tablet approaches, and may incorporate, in one dosage form, the benefits of both these drug delivery systems.

In its most basic form, PRODAS involves the direct compression of an immediate release granulate to produce individual mini tablets that contain an active agent. These mini tablets are subsequently incorporated into hard gels and capsules that represent the final dosage form. A more beneficial use of this technology is in the production of controlled release formulations. In this case, the incorporation of various polymer combinations within the granulate may delay the release rate of drugs from each of the individual mini tablets. These mini tablets may subsequently be coated with controlled release polymer solutions to provide additional delayed release properties. The additional coating may be necessary in the case of highly water soluble drugs or drugs that are perhaps gastroirritants where release can be delayed until the formulation reaches more distal regions of the gastrointestinal tract. One value of PRODAS technology lies in the inherent flexibility to formulation whereby combinations of mini tablets, each with different release rates, are incorporated into one dosage form. As well as potentially permitting controlled absorption over a specific period, this also may permit targeted delivery of drug to specific sites of absorption throughout the gastrointestinal tract. Combination products also may be possible using mini tablets formulated with different active ingredients.

DUREDAS is a bilayer tableting technology that may be used to formulate an active agent. DUREDAS was developed to provide for two different release rates, or dual release of a drug from one dosage form. The term bilayer refers to two separate direct compression events that take place during the tableting process. In an exemplary embodiment, an immediate release granulate is first compressed, being followed by the addition of a controlled release element which is then compressed onto this initial tablet. This may give rise to the characteristic bilayer seen in the final dosage form.

The controlled release properties may be provided by a combination of hydrophilic polymers. In certain cases, a rapid release of an active agent may be desirable in order to facilitate a fast onset of therapeutic affect. Hence one layer of the tablet may be formulated as an immediate-release granulate. By contrast, the second layer of the tablet may release the drug in a controlled manner, e.g., through the use of hydrophilic polymers. This controlled release may result from a combination of diffusion and erosion through the hydrophilic polymer matrix.

A further extension of DUREDAS technology is the production of controlled release combination dosage forms. In this instance, two different active agents may be incorporated into the bilayer tablet and the release of drug from each layer controlled to maximize therapeutic effect of the combination.

An active agent can be incorporated into any one of the aforementioned controlled released dosage forms, or other conventional dosage forms. The amount of active agent contained in each dose can be adjusted, to meet the needs of the individual patient, and the indication. One of skill in the art and reading this disclosure will readily recognize how to adjust the level of active agent and the release rates in a controlled release formulation, in order to optimize delivery of an active agent and its bioavailability.

Inhalational Formulations

An active agent will in some embodiments be administered to a patient by means of a pharmaceutical delivery system for the inhalation route. An active agent may be formulated in a form suitable for administration by inhalation. The inhalational route of administration provides the advantage that the inhaled drug can bypass the blood-brain barrier. The pharmaceutical delivery system is one that is suitable for respiratory therapy by delivery of an active agent to mucosal linings of the bronchi. An active agent can be delivered by a system that depends on the power of a compressed gas to expel the active agent from a container. An aerosol or pressurized package can be employed for this purpose.

As used herein, the term "aerosol" is used in its conventional sense as referring to very fine liquid or solid particles carries by a propellant gas under pressure to a site of therapeutic application. When a pharmaceutical aerosol is employed, the aerosol contains an active agent, which can be dissolved, suspended, or emulsified in a mixture of a fluid carrier and a propellant. The aerosol can be in the form of a solution, suspension, emulsion, powder, or semi-solid preparation. Aerosols employed in a method of the present disclosure are intended for administration as fine, solid particles or as liquid mists via the respiratory tract of a patient. Various types of propellants known to one of skill in the art can be utilized. Suitable propellants include, but are not limited to, hydrocarbons or other suitable gas. In the case of the pressurized aerosol, the dosage unit may be determined by providing a value to deliver a metered amount.

An active agent can also be formulated for delivery with a nebulizer, which is an instrument that generates very fine liquid particles of substantially uniform size in a gas. For example, a liquid containing an active agent is dispersed as droplets. The small droplets can be carried by a current of air through an outlet tube of the nebulizer. The resulting mist penetrates into the respiratory tract of the patient.

A powder composition containing an active agent, with or without a lubricant, carrier, or propellant, can be administered to a mammal in need of therapy. This embodiment can be carried out with a conventional device for administering a powder pharmaceutical composition by inhalation. For example, a powder mixture of the active agent and a suitable powder base such as lactose or starch may be presented in unit dosage form in for example capsular or cartridges, e.g. gelatin, or blister packs, from which the powder may be administered with the aid of an inhaler.

There are several different types of inhalation methodologies which can be employed in connection with the present disclosure. An active agent can be formulated in basically three different types of formulations for inhalation. First, an active agent can be formulated with low boiling point propellants. Such formulations are generally administered by conventional meter dose inhalers (MDI's). However, conventional MDI's can be modified so as to increase the ability to obtain repeatable dosing by utilizing technology which measures the inspiratory volume and flow rate of the patient as discussed within U.S. Pat. Nos. 5,404,871 and 5,542,410.

Alternatively, an active agent can be formulated in aqueous or ethanolic solutions and delivered by conventional nebulizers. In some embodiments, such solution formulations are aerosolized using devices and systems such as disclosed within U.S. Pat. Nos. 5,497,763; 5,544,646; 5,718,222; and 5,660,166.

An active agent can be formulated into dry powder formulations. Such formulations can be administered by simply inhaling the dry powder formulation after creating an aerosol mist of the powder. Technology for carrying such out is described within U.S. Pat. No. 5,775,320 issued Jul. 7, 1998 and U.S. Pat. No. 5,740,794 issued Apr. 21, 1998.

Dosages

Although the dosage used will vary depending on the clinical goals to be achieved, a suitable dosage range is one which provides up to about 1 µg to about 1,000 µg or about 10,000 µg of an active agent and can be administered in a single dose. Alternatively, a target dosage of an active agent can be considered to be about in the range of about 0.1-1000 µM, about 0.5-500 µM, about 1-100 µM, or about 5-50 µM in a sample of host blood drawn within the first 24-48 hours after administration of the agent.

In some cases, a suitable dosage is one that provides a total daily dose of from about 0.1 mg to about 500 mg, from about 0.1 mg to about 5 mg, from about 0.1 mg to about 50 mg, from about 5 mg to about 10 mg, from about 10 mg to about 50 mg, from about 50 mg to about 100 mg, or from about 100 mg to about 500 mg.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

In some embodiments, multiple doses of an active agent are administered. The frequency of administration of an active agent can vary depending on any of a variety of factors, e.g., severity of the symptoms, etc. For example, in some embodiments, an active agent is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). In some embodiments, an active agent is administered continuously.

The duration of administration of an active agent, e.g., the period of time over which an active agent is administered, can vary, depending on any of a variety of factors, e.g., patient response, etc. For example, an active agent can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more. In some embodiments, an agent is administered for the remaining lifetime of the individual.

In some embodiments, administration of an active agent is discontinuous, e.g., an active agent is administered for a first period of time and at a first dosing frequency; administration of the active agent is suspended for a period of time; then the active agent is administered for a second period of time for a second dosing frequency. The period of time during which administration of the active agent is suspended can vary depending on various factors, e.g., overall health status of the individual; and will generally range from about 1 week to about 6 months, e.g., from about 1 week to about 2 weeks, from about 2 weeks to about 4 weeks, from about one month to about 2 months, from about 2 months to about 4 months, or from about 4 months to about 6 months, or longer. The first period of time may be the same or different than the second period of time; and the first dosing frequency may be the same or different than the second dosing frequency.

Routes of Administration

An active agent is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, subcutaneous, intradermal, topical application, intravenous, rectal, nasal, oral and other enteral and parenteral routes of administration. Routes of administration may be combined, if desired, or adjusted depending upon the agent and/or the desired effect. The active agent can be administered in a single dose or in multiple doses. In some embodiments, the active agent is administered orally. In other specific embodiments, the active agent is administered via intravenous administration (e.g., by injection). In other embodiments, the active agent is administered intramuscularly. In other embodiments, the active agent is administered at or near a treatment site.

The active agent can be administered to a host using any available conventional methods and routes suitable for delivery of conventional drugs, including systemic or localized routes. In general, routes of administration contemplated by the present disclosure include, but are not necessarily limited to, enteral, parenteral, and inhalational routes.

Parenteral routes of administration other than inhalation administration include, but are not necessarily limited to, topical, transdermal, subcutaneous, intramuscular, intraorbital, intracapsular, intraspinal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The active agent can also be delivered to the subject by enteral administration. Enteral routes of administration include, but are not necessarily limited to, oral and rectal (e.g., using a suppository) delivery.

Methods of administration of the active agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

Subjects Suitable for Treatment

Subjects suitable for treatment using a method of the present disclosure include subjects having a disease or disorder associated with elevated tissue or fluid levels of lactate. Subjects suitable for treatment using a method of the present disclosure include subjects having elevated tissue or fluid levels of lactate. Subjects suitable for treatment using a method of the present disclosure include subjects identified as having elevated tissue or fluid levels of lactate.

In some cases, a subject suitable for treatment using a method of the present disclosure has lactic acidosis. In some cases, a subject suitable for treatment using a method of the present disclosure has lactic acidosis and has diabetes mellitus, e.g., has been diagnosed as having diabetes mellitus. In some cases, a subject suitable for treatment using a method of the present disclosure has lactic acidosis resulting from treatment with an anti-hyperglycemic acid, e.g., a biguanide. In some cases, a subject suitable for treatment using a method of the present disclosure has lactic acidosis caused by metformin (N,N-dimethylimidodicarbonimidic diamide) treatment. In some cases, a subject suitable for treatment using a method of the present disclosure has lactic acidosis caused by metformin overdose.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

In this report, data are presented showing that 5-amino-2-hydroxymethylphenyl boronic acid (ABA) can directly decrease blood lactate levels, via its ability to complex extracellular lactate and increase its membrane permeability, resulting in enhanced intracellular metabolism. ABA binds lactate with a Kd of 0.01 and increases its Log D from −2 to 0.5 thereby increasing its membrane permeability. The data presented demonstrate that ABA can bind lactate in mice and lower extracellular lactate concentrations from 2 mM to 0.7 mM. In addition the data demonstrate that ABA can rescue mice from metformin induced acidosis, and was able to decrease extracellular lactate concentrations from 10 mM to 2 mM and normalize blood pH from 6.6 to 7.2. ABA is the first class of molecules that can directly decrease the blood lactate concentration, and therefore has the potential to have a significant impact on medicine, given the large number of diseases that are caused by elevated lactate levels in the blood.

Materials and Methods 5-amino-2-hydroxymethylphenyl boronic acid (ABA) was purchased from Combi-Blocks Inc., sodium L-lactate was purchased from Sigma Aldrich, metformin was purchased from Sigma Aldrich, blood lactate meter was purchased from Nova Biomedical, pyruvate, glutamate and lactate assay kit was purchased from Abcam Inc., phosphate buffer saline (PBS) was purchased from VWR, syringes, needles pipette tips and eppendorf tubes were purchased from VWR, nuclear magnetic resonance (NMR) tubes were purchased from VWR, 400 MHz Bruker NMR was utilized to obtain the $^{11}$B and $^{13}$C traces, fisher Scientific accumet basic was utilized to measure pH, HepG2 cells were obtained from the biosciences divisional services at UC Berkeley, cell counting kit-8 for cell survival was purchased from Dojindo Molecular Diagnostics Inc. and absorbance measurements were performed using a Tecan i4 microplate reader.

Log D Measurements:

ABA enhances the log D of lactate thereby making it cell membrane permeable. 45 μmoles of ABA and 3-$^{13}$C-sodium L-lactate dissolved in 500 μL of 1×PBS at pH 7.4 were added to 500 μL of octanol and vigorously shaken for 16 h and then centrifuged for 2 min at 10,000×Gs to extract PBS. A 200 μL of D$_2$O along with 188.7 μmoles (10 μL of 99.8%) of acetonitrile was added to the PBS and a carbon NMR was performed with 16 scans. The area under the curve for the NMR traces obtained was calculated using Mest-ReC software. Similarly, a carbon NMR was performed with 16 scans on a solution containing 45 μmoles of ABA, 45 μmoles of 3-$^{13}$C-sodium L-lactate dissolved in 500 μL of 1×PBS at pH 7.4 along with 200 μL of D$_2$O and with 188.7 μmoles (10 μL of 99.8%) of acetonitrile. Area under the curve for the NMR traces obtained was calculated using Mest-ReC software. Acetonitrile peak at δ=1.47 was used as reference.

Log D of ABA-lactate complex was found to be 0.5 using the following formula:

$$\mathrm{Log}D = \mathrm{Log}\left(\frac{\text{Area under the curve of } PBS \text{ before extraction} - \text{Area under the curve of } PBS \text{ after extraction}}{\text{Area under the curve of } PBS \text{ after extraction}}\right)$$

Furthermore, as controls, 3-$^{13}$C-sodium L-lactate dissolved in 500 μL of 1×PBS at pH 7.4 was added to 500 μL of octanol and vigorously shaken for 16 h and then centrifuged for 2 min at 10,000×Gs to extract PBS. A 200 μL of D$_2$O along with 188.7 μmoles (10 μL of 99.8%) of acetonitrile was added to the PBS and a carbon NMR was performed with 16 scans. The area under the curve for the NMR traces obtained was calculated using Mest-ReC software. Similarly, a carbon NMR was performed with 16 scans on a solution containing 45 μmoles of 3-$^{13}$C-sodium L-lactate dissolved in 500 μL of 1×PBS at pH 7.4 along with 200 μL of D$_2$O and with 188.7 μmoles (10 μL of 99.8%) of acetonitrile. Area under the curve for the NMR traces obtained was calculated using Mest-ReC software.

Log D of lactate was found to be −2 using the following formula:

$$\mathrm{Log}D = \mathrm{Log}\left(\frac{\text{Area under the curve of } PBS \text{ before extraction} - \text{Area under the curve of } PBS \text{ after extraction}}{\text{Area under the curve of } PBS \text{ after extraction}}\right)$$

General Cell Culture Methodology:

Liver hepatocellular carcinoma (HepG2) cell line was utilized for all the experiments. The cells were plated in a T-25 flask (VWR) at 1×10$^6$ cells in 10 mL volume. All the experiments were performed at the cell passage number 2-5. Cells were passaged every 3$^{rd}$ day. A 3 mL of 0.05% trypsin solution (VWR) was added to the cells and incubated at 37° C. for 2-4 minutes. Cells were removed from the flask and added to 10 mL of cell culture media (10% fetal bovine serum in DMEM-VWR) to neutralize the trypsin. The cell pellet was resuspended in cell culture media and counted using a hemocytometer and trypan staining (Fisher Scientific). The cells were then seeded in a 96 well plate in 100 μL cell culture media at 10,000 cells/well. The cells were allowed to grow for 1 day before use in an experiment.

Jurkat T-cells and Ramos B-cells were cultured in a T-25 flask at 1×10$^6$ cells in 10 mL volume. All the experiments were performed at the cell passage number 2-5. Cells were passaged every 3$^{rd}$ day. T-cells and B-cells being suspension cells, were pipette out and centrifuged to remove the media. The cells were resuspended in 10 mL media and counted using a hemocytometer and trypan staining (Fisher Scientific). The cells were then added to sterile eppendorf tubes with 200 media and the pyruvate and glutamate assay experiments were performed in the eppendorf tubes.

Raw 264.7 macrophages were cultured in a T-25 flask at 1×10$^6$ cells in 10 mL volume. All the experiments were performed at the cell passage number 2-5. Cells were passaged every 3$^{rd}$ day. Cells were scrapped using a cell scrapper and centrifuged to remove the media. The cells were resuspended in 10 mL media and counted using a hemocytometer and trypan staining (Fisher Scientific). The cells were then seeded in a 96 well plate in 100 μL cell culture media at 10,000 cells/well. The cells were allowed to grow for 1 day before use in an experiment.

Intracellular Pyruvate and Glutamate with Varying Concentration of ABA-Lactate Complex:

Intracellular pyruvate and glutamate levels are based on lactate metabolism during the Kreb's cycle. To investigate if ABA can increase the metabolism of lactate into intracellular pyruvate and glutamate upon complexing with extracellular lactate, HepG2 cells were seeded in a 96 well plate in 100 μL cell culture media at 10,000 cells/well and cultured overnight. Cell culture media was aspirated and washed twice with sterile PBS, by adding 100 μL of PBS and aspirating it. In some cases, the monocarboxylate transporter was inhibited with 50 μL of 10 mM α-cyano-4-hydroxycinnamate (CNC) (or PBS for controls). 50 μL of 10 mM, 20 mM or 30 mM sodium lactate made in PBS was added to the cells in triplicate. Furthermore, 20 mM, 40 mM or 60 mM sodium L-lactate was mixed with 20 mM, 40 mM or 60 mM of ABA and 50 of this solution was added to separate set of wells containing CNC or PBS. 50 μL of 10 mM, 20 mM or 30 mM of ABA was also added to the wells containing 50 μL of CNC or 50 μL of PBS. Therefore, final concentration of 5 mM CNC, along with 5 mM, 10 mM and 15 mM ABA-lactate or lactate was achieved. Cells with 100 μL of PBS were considered as the no treatment negative control. These cells were incubated at 37° C. for 30 min and the supernatant was aspirated. 50 μL of 0.1% triton x-100 was added to the cells and glutamate and pyruvate assay was performed according to the manufacturer's directions. The absorbance generated was read using a plate reader at 450 nm for glutamate and 570 nm for pyruvate. The values were normalized with no treatment controls and plotted (FIGS. 3A, 3B, 5A, and 5B).

ABA and Blood Lactate Levels:

ABA can modulate the blood lactate levels by binding lactate and enhancing its metabolism. 11 μmoles of ABA in 50 μL of 1×PBS, where pH was normalized to 7.4 was injected via tail vein injection. Mice were sacrificed and cardiac puncture was utilized to extract the blood. Lactate assay kit was utilized to measure the lactate in the blood diluted 100 fold in PBS (FIG. 4A) according to the manufacturer's direction.

Figure 4A:
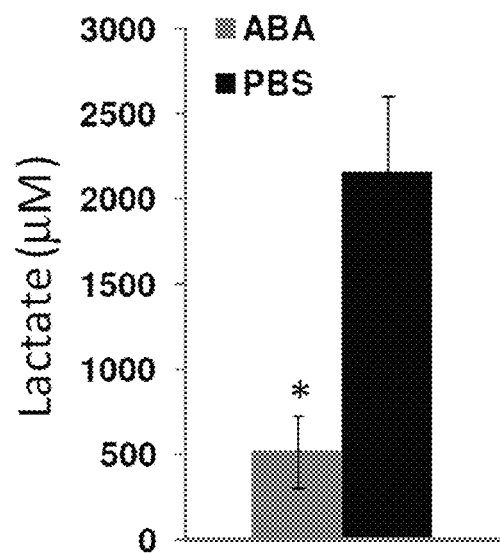
FIGS. 4A-D depict the effect of ABA on blood lactate levels, pH, and glutamate levels.
Figure 4B:
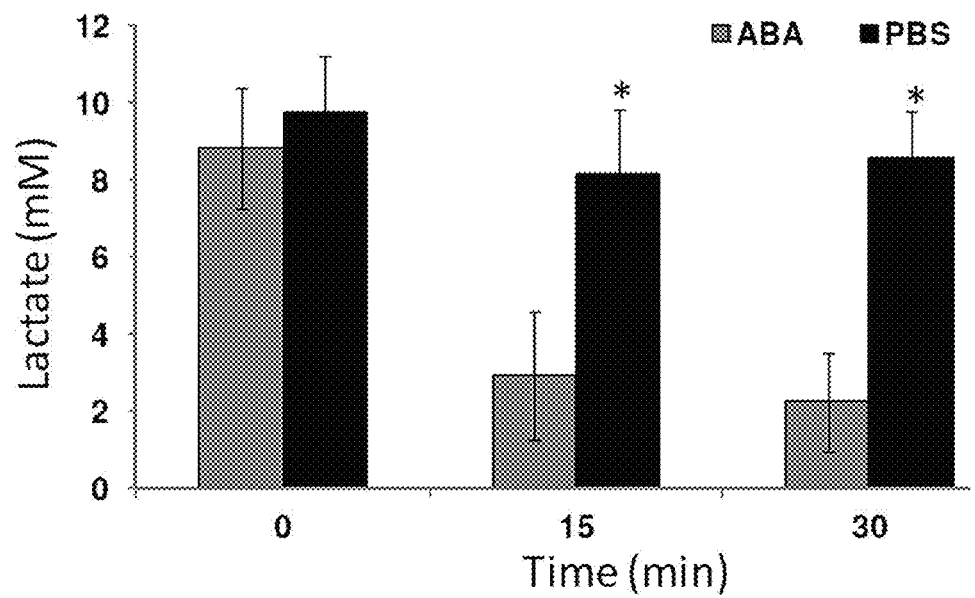
Figure 4C:
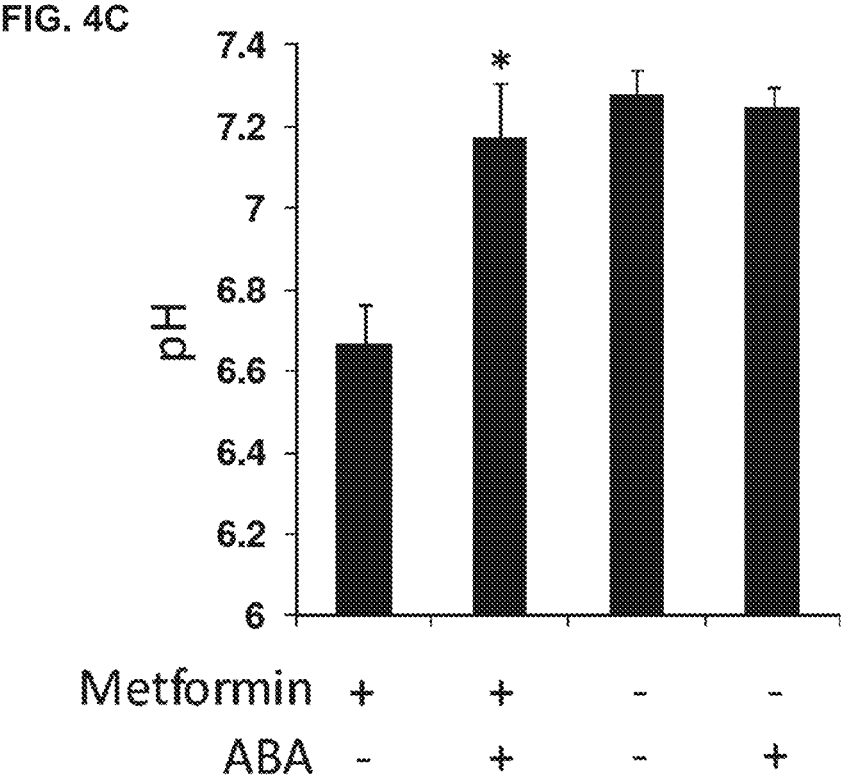
Figure 4D:
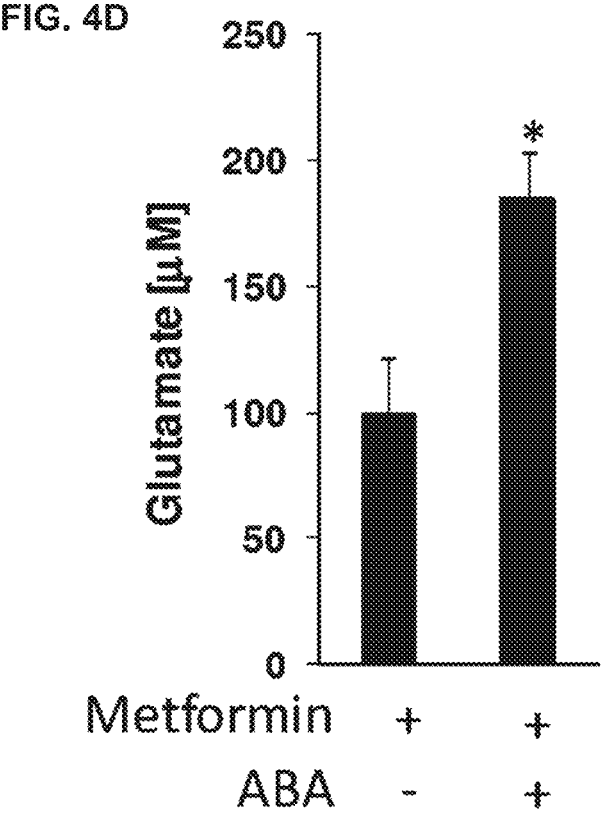

ABA in Lactic Acidosis Animal Model:

Metformin induced lactic acidosis animal model was utilized to test the efficacy of ABA to reduce the blood lactate levels. Female 6-8 weeks old C57Bl6/j mice purchased from Jackson Laboratories were weighed and injected with 400 mg/kg of metformin made in 500 µL 1×PBS. Once the arterial lactate levels of mice reached 10 mM (~2 h), mice were injected with either 11 µmoles of ABA in 50 µL of 1×PBS (pH=7.4) via tail vein or with 50 µL of 1×PBS as control. Mice were sacrificed at 0, 15 and 30 min after treatment and cardiac puncture was utilized to extract the blood. 100 µL of the blood was centrifuged immediately at 10,000×Gs for 10 min to obtain the plasma. Lactate and glutamate assay kit was utilized to measure the lactate and glutamate levels in the blood (FIGS. 4B and 4D). Furthermore, blood obtained via cardiac puncture was also utilized to measure the whole blood pH (FIG. 4C).

Statistical Analysis:

Statistical analyses were performed using student's t-test and p-values for each experiment were determined Statistically significant data ($p<0.05$) are depicted using the '*' symbol.

Results

In this report, a strategy is presented for treating lactic acidosis based on the compound ABA, which reversibly complexes with lactate and increases lactate metabolism by enhancing lactate's membrane permeability (FIG. 1). ABA is selective toward lactate because of the ortho-hydroxyl group on the benzene ring which makes the boron susceptible to attack by the carboxyl group of lactate followed by ring closure via the hydroxyl group. Lactate complexed with ABA passively enters cells due to the hydrophobicity of ABA, and become metabolized into pyruvate and glutamate via the Kreb's cycle, resulting in detoxification of extracellular lactate. ABA based therapy also normalizes blood pH because the ABA-lactate complex makes lactate membrane permeable, dissipating the extracellular-intracellular lactate gradients which are required for MCT1 (also known as monocarboxylate transporter 1; solute carrier family 16 member 1; and SLC16A1) based blood acidification.

Figure 2A:
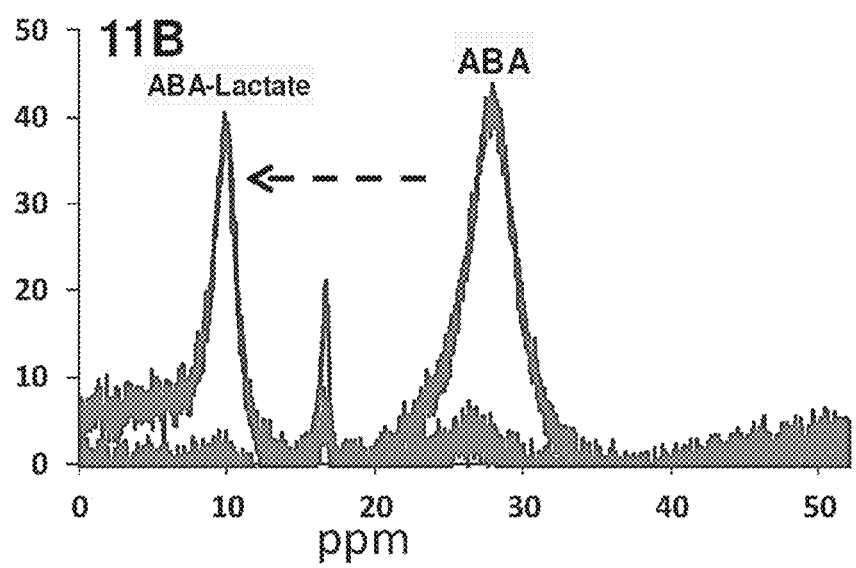
FIGS. 2A-B depict binding of ABA to lactate.

ABA Binds Lactate with Specificity:

To investigate whether ABA can selectively bind lactate in the presence of serum and other metabolites, ABA binding to lactate was measured using boron nuclear magnetic resonance (NMR) experiments. 11 µmoles of ABA and sodium L-lactate were added to 500 µL of 10% fetal bovine serum in Dulbecco's Modified Eagle Medium (DMEM) and analyzed by boron NMR. As a control, 11 µmoles of ABA (without lactate) was dissolved in 500 µL of 10% fetal bovine serum in Dulbecco's Modified Eagle Medium (DMEM) and $^{11}$B boron NMR was performed. FIG. 2A demonstrates that ABA bound L-lactate in the presence of serum and other metabolites. For example, the aromatic boron of ABA in serum by itself had a peak at $\delta=29$ and this shifted to $\delta=9$ in the presence of lactate and serum.

Figure 2B:
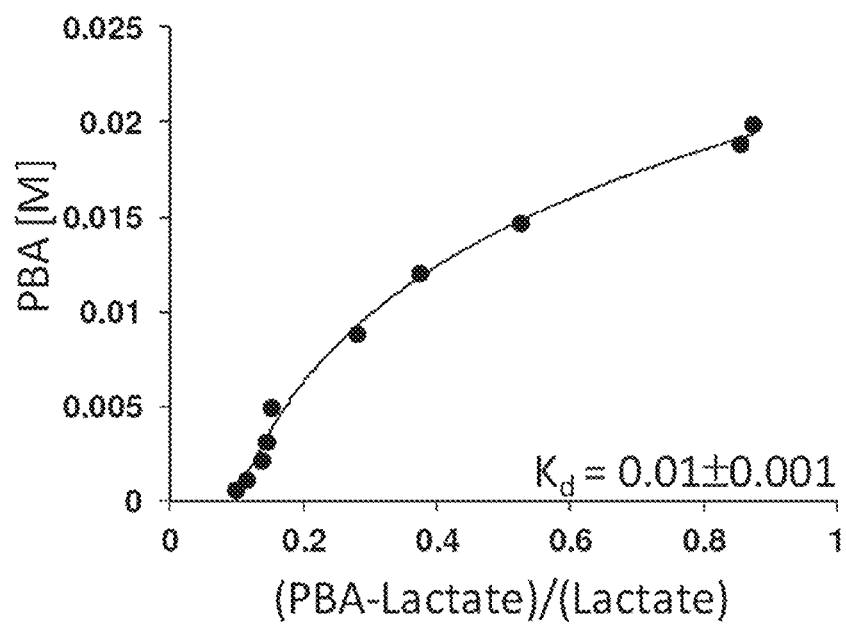

Dissociation Constant of ABA-Lactate Complex:

ABA binds lactate in water and serum solutions, however the affinity of ABA toward lactate was not known. $^{13}$C carbon NMR was used to determine the dissociation constant of the reversible ABA-lactate complex. ABA made in $D_2O$ at concentrations varying from 0 to 20 mM was added to 134 mM solution of 3-$^{13}$C sodium L-lactate in a NMR tube and NMR spectra were obtained. A peak shift from $\delta=21.6$ to $\delta=20.1$ was observed in the spectra. The ratio of the area under the curve of the peak $\delta=21.6$ corresponding to free 3-$^{13}$C sodium L-lactate and area under the curve of peak $\delta=20.1$ corresponding to ABA-lactate complex was obtained (x-axis) and plotted against the concentration of ABA (y-axis). A logarithmic curve was fitted to the data (FIG. 2B). The dissociation constant (Kd) was obtained by dividing the concentration of ABA with the corresponding ratio of the area under the peak of ABA-lactate complex to lactate. A total of 3 runs were performed to obtain statistics. The dissociation constant of the ABA-lactate complex was determined by $^{13}$C NMR to be 0.015±0.003. The reversible binding of extracellular lactate makes lactate available for its oxidation into pyruvate by intracellular enzymes.

ABA is Membrane Permeable:

It was investigated whether ABA can enhance lactate membrane permeability. Liposomes were generated from 1,2-dimyristoyl-sn-glycero-3-phosphocholine (DMPC), by evaporating 400 µL of 1 mg/mL of DMPC in chloroform in a 100 mL glass flask to completion; and the lipids were re-suspended in 400 µL PBS, thereby forming the liposomes. 50 µL of the liposomes and 50 µL of 112 mM ABA premixed with lactate were then added to the wells of the 96-well plate, and lactate assay kit was performed, according to the manufacturer's instructions. As controls, 50 µL of PBS and 50 µL of 112 mM ABA premixed with lactate were then added to the wells of the 96-well plate and lactate assay kit was performed, according to the manufacturer's instructions. Furthermore, for determining the permeability of lactate through the liposomes, 50 µL of the liposomes and 50 µL of 112 mM lactate were added to the wells of the 96-well plate, and lactate assay kit was performed, according to the manufacturer's instructions. As controls, 50 µL of PBS and 50 µL of 112 mM lactate were added to the wells of the 96-well plate and lactate assay kit was performed, according to the manufacturer's instructions. The fact that ABA-lactate permeates through the liposomes was demonstrated by a dramatic decrease of 80% in the amount of lactate present in the extra-liposomal space for the enzymatic reaction, whereas lactate by itself did not permeate through the liposomes as observed by a modest change in the amount of lactate present for the enzymatic reaction.

Importantly, ABA-lactate complex passively diffuses into a cell because of the dramatic change in hydrophobicity of lactate upon binding to ABA, as measured by increased log D of lactate from −2 to 0.5. In the intracellular space lactate dissociates from ABA-lactate complex and is metabolized by lactate dehydrogenase into pyruvate and other downstream metabolites.

Effect on Intracellular Pyruvate and Glutamate Levels

Figure 5A:
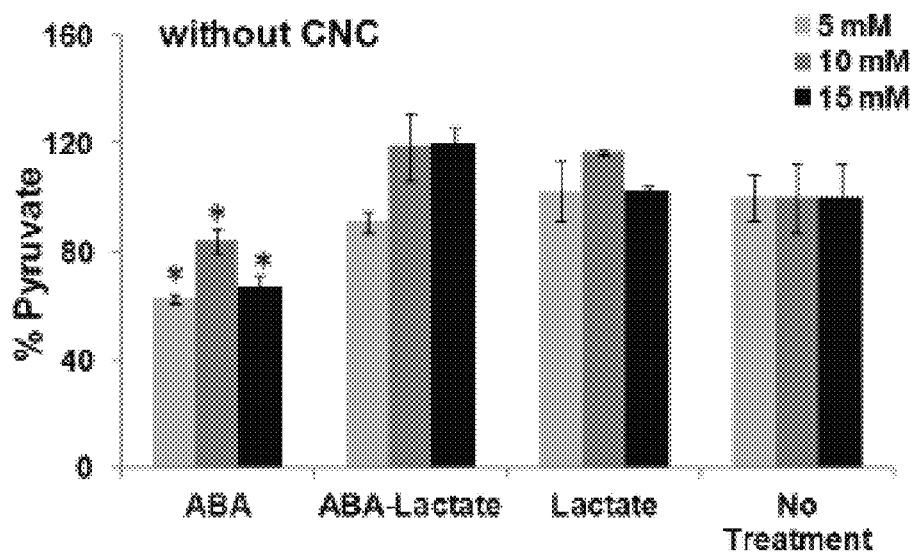
FIGS. 5A-B depict the effect of ABA on pyruvate levels and glutamate levels.
Figure 5B:
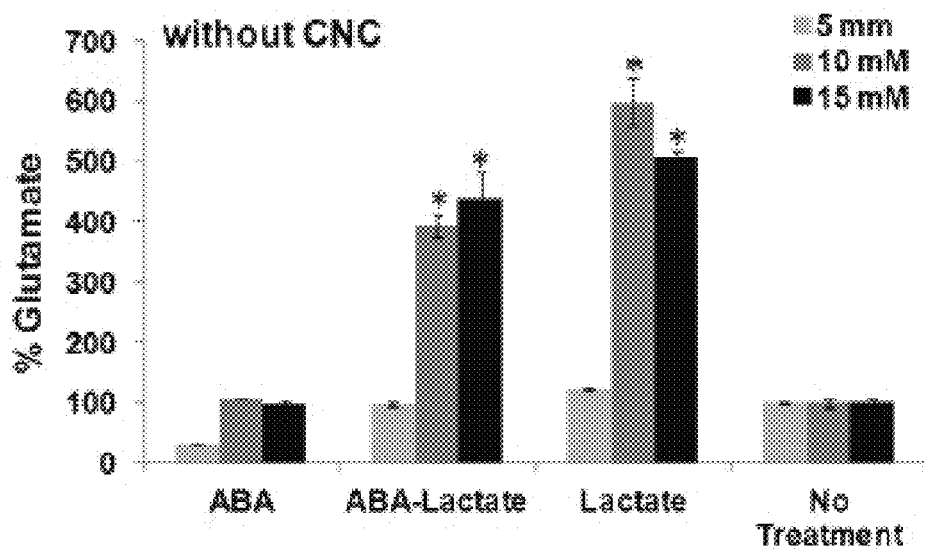

ABA binds lactate, passively permeates into all cells of the body and increases the metabolism of lactate. Investigations were performed to determine if ABA added to cells treated with lactate could enhance the metabolism of extracellular lactate into intracellular pyruvate and glutamate. 5 mM, 10 mM, or 15 mM of ABA, lactate, or ABA-lactate were added to macrophages, T-cells, B-cells and HepG2 cells, and intracellular levels of pyruvate and glutamate, which are the downstream metabolite products of the Kreb's cycle, were quantified. The experiments were performed in the presence (FIG. 3) or absence (FIG. 5) of 5 mM α-cyano-4-hydroxycinnamate (CNC), a monocarboxylate transporter (MCT) inhibitor. Monocarboxylate transporter (MCT) isoforms 1-4 catalyze the proton-linked transport of monocarboxylates such as L-lactate across the plasma membrane FIGS. 3A, 3B, 5A and 5B demonstrate that an increase in extracellular ABA-lactate complex is able to increase the amount of intracellular pyruvate and glutamate levels (i.e., increase catabolism of lactate to intracellular pyruvate and glutamate). In the absence of the MCT inhibitor (CNC), ABA-lactate complex enhanced the production of intracellular glutamate, which was significantly higher than no treatment control but lower than lactate at 10 mM and 15 mM (FIGS. 5A and 5B). However, ABA-lactate complex did not modulate the intracellular pyruvate levels in the absence of MCT inhibitor, due to the pyruvate equilibrium established by the MCT.

Figure 3A:
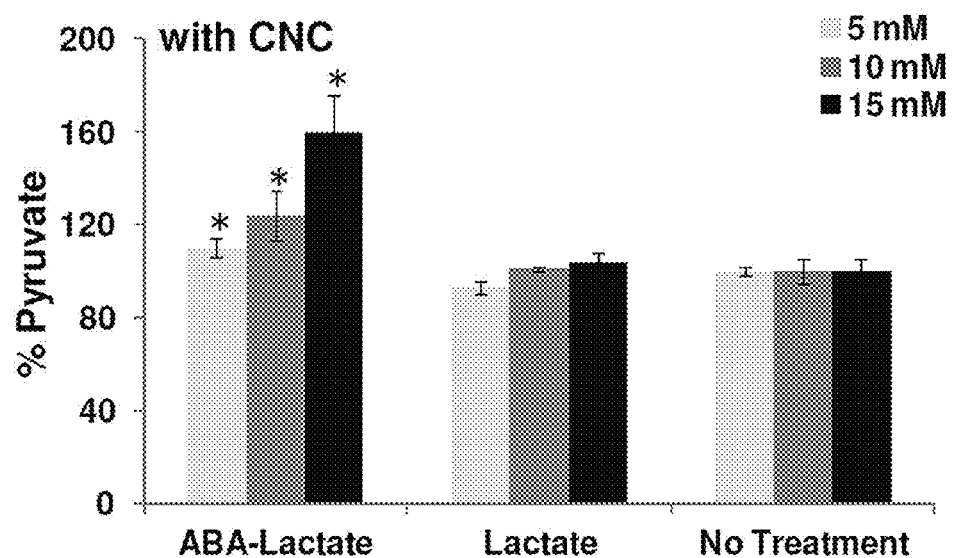
FIGS. 3A-B depict the effect administering ABA on production of pyruvate and glutamate.
Figure 3B:
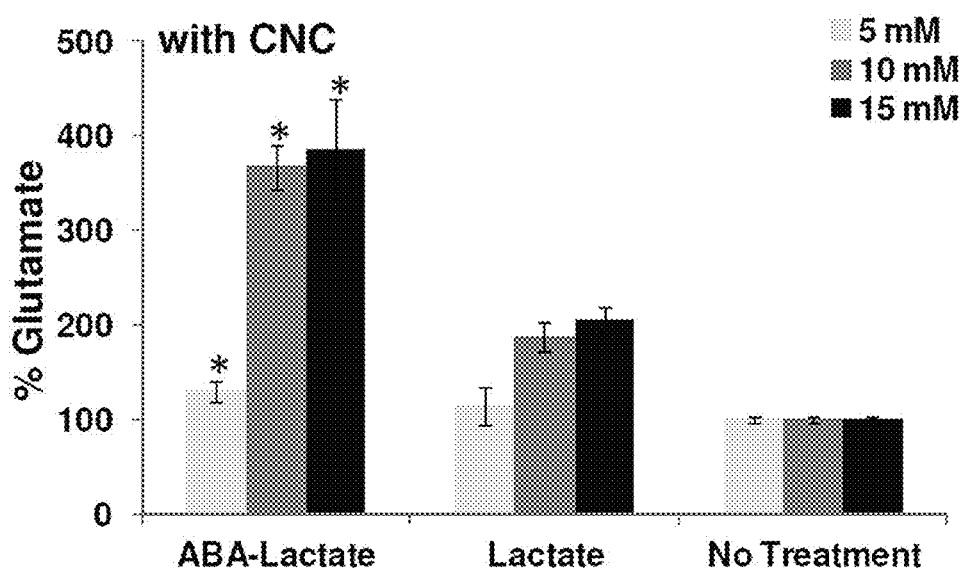

In the presence of the MCT inhibitor (CNC), ABA-lactate complex enhanced intracellular pyruvate and glutamate levels as compared to cells receiving only lactate (FIGS. 3A and 3B). These data suggest that ABA-lactate is passively transported into the cells and due to dissociation of lactate from ABA, lactate is utilized by the cells' Kreb's cycle to generate pyruvate and glutamate.

Effect on Blood Lactate Levels and Blood pH In Vivo

There is a great interest in decreasing blood lactate levels during lactic acidosis, because elevated blood lactate causes a decrease in blood pH, which has numerous pathological effects such as globally changing enzyme activity, reducing blood pressure and causing apoptosis, which collectively causes significant morbidity. Elevated blood lactate is difficult to decrease because it is difficult to either change its rate of consumption or rate of production because it is membrane impermeable and there is no metabolism of lactate in the extracellular space, and inhibiting its production requires inhibiting the Kreb's cycle which is toxic. ABA has the potential to significantly improve the treatment of lactic acidosis because it can potentially increase its rate of consumption and thereby lower its blood concentration in a non-toxic manner.

ABA was therefore tested for its ability to bind lactate in vivo and decrease blood lactate levels. 11 µmoles of ABA in 100 µL of saline was injected into mice via the tail vein and after 10 min their blood was analyzed for lactate and compared against controls. FIG. 4A demonstrates that ABA can reduce blood lactate levels, for example, the blood lactate levels in a healthy mouse were 2±1.5 mM, while mice treated with ABA had a 3 fold reduction in blood lactate levels, down to 776±30 µM. In addition, ABA can potentially modulate extracellular lactate levels by two methods, either by enhanced excretion through kidneys or via increased membrane permeability and metabolism. Importantly, ABA showed no toxicity to the mice at the dose used for modulation of lactate levels.

There are numerous applications of a compound that can decrease extracellular lactate. For example, there is a great need to generate a treatment for lactic acidosis caused by metformin overdose which inhibits gluconeogenesis and causes mortality in 50% of the cases.

Figure 6:
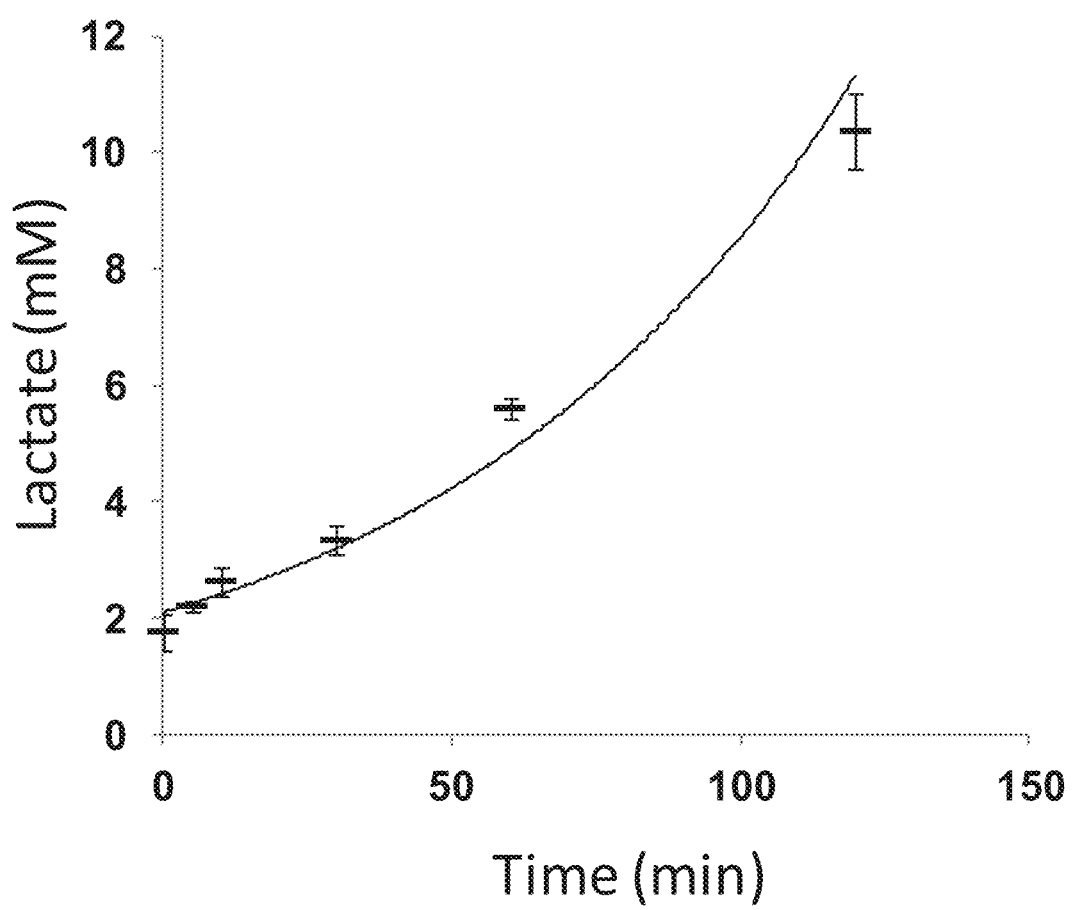
FIG. 6 depicts the effect of intraperitoneal injection of ABA on blood lactate levels.

A metformin induced lactic acidosis animal model was utilized to test the efficacy of ABA to reduce the blood lactate levels. Female 6-8 weeks old C57Bl6/j mice purchased from Jackson Laboratories were weighed and injected intraperitoneally with 400 mg/kg of metformin made in 500 µL 1×PBS. Mice were returned to their cages and arterial blood lactate was measured via the tail snip at 5, 15, 30, 60 and 120 min using a blood lactate meter (FIG. 6).

ABA was then tested for its ability to rescue mice from metformin induced lactic acidosis by detoxifying extracellular lactate. Lactic acidosis induced in mice by intraperitoneal injection of 400 mg/kg metformin in saline, were injected with ABA via tail vein injection and after sacrificing mice after 90 min blood pH levels, lactate and glutamate levels were analyzed. FIG. 4B demonstrates that ABA can bring the blood lactate to normal levels in metformin-induced lactic acidosis mouse model by binding lactate and enhancing its metabolism in vivo. For example, mice injected with 11 µmoles of ABA decreased the blood lactate levels to 2±1.5 mM whereas the control mice which received saline had arterial blood lactate levels of 10±1.5 mM. pH is a great indicator of healthy blood physiology. It was therefore investigated if ABA modulates arterial blood pH levels in mice suffering from lactic acidosis. FIG. 4C demonstrates that mice receiving 11 µmoles of ABA had a higher blood pH (7.18±0.13) than mice receiving saline as control (6.67±0.09).

This shows that ABA is able to restore pH balance in the blood of mice suffering from lactic acidosis, an important indicator of survival. Furthermore, blood glutamate levels were two times higher in the lactic acidosis mice treated with 11 µmoles of ABA as compared to the mice treated with saline (FIG. 4D), which signifies that ABA is able to bind and enhance lactate metabolism in vivo thereby restoring the lactate homeostasis. Therefore, increased lactate metabolism in vivo and restoration of pH balance by ABA, can lead to a better prognosis of patients suffering from lactic acidosis. In addition to metformin associated lactic acidosis, ABA can have a great impact on the field of cancer metabolomics where lactate plays a central role in disease pathophysiology.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of reducing the level of lactate in a fluid or tissue of an individual, the method comprising administering to the individual an effective amount of:

a) a compound of formula I:

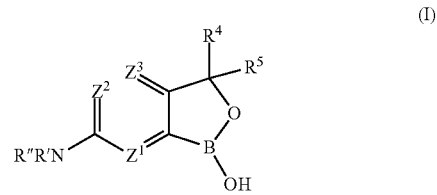

(I)

wherein $Z^1$ is CH, $CR^1$ or N;

$Z^2$ is CH, $CR^2$ or N;

$Z^3$ is CH, $CR^3$ or N;

$R^1$, $R^2$, $R^3$, $R^4$ and $R^5$ are each independently selected from hydrogen, acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$— substituted alkyl, —$SO_2$-aryl, —$SO_2$-heteroaryl and trihalomethyl; and R' and R" are each independently selected from hydrogen, an alkyl, an aryl, substituted alkyl and substituted aryl; or b) a pharmaceutical composition comprising a compound of (a), and determining the level of lactate in a fluid or tissue of the individual;

wherein said administering reduces the level of lactate in a fluid or tissue in the individual.

2. The method of claim 1, wherein the fluid is blood or a blood fraction.

3. The method according to claim 1, wherein the individual is a mammal.

4. The method according to claim 1, wherein the individual is a human.

5. The method according to claim 1, wherein an effective amount of the compound is in a range of from 10 µM to 500 mM.

6. The method according to claim 1, wherein said administering reduces the level of lactate in a fluid or tissue in the individual to less than 5 mM.

7. The method according to claim 1, wherein said administering increases the blood pH of the individual by at least 0.02 pH units.

8. The method according to claim 1, wherein the compound is administered in combination with an anti-cancer agent.

9. The method according to claim 8, wherein the anti-cancer agent is a cancer chemotherapeutic agent.

10. The method of claim 1,
wherein the compound selectively binds to lactate and reduces the level of lactate in a tissue or fluid in the individual, thereby treating a disease or disorder associated with elevated lactate in the individual.

11. The method of claim 10, wherein the tissue or fluid is blood or a blood fraction.

12. The method according to claim 10, wherein the disease or disorder is lactic acidosis.

13. The method according to claim 10, wherein the disease or disorder is cancer, non-Hodgkin's lymphoma, Burkitt lymphoma, mitochondrial encephalomyopathy, lactic acidosis and stroke-like episodes (MELAS), diabetes mellitus and deafness (DAD), maternally inherited diabetes and deafness (MIDD), glucose-6-phosphatase deficiency, glycogen storage disease type I (GSD I), von Gierke's disease, fructose 1,6-diphosphatase deficiency, pyruvate dehydrogenase deficiency (PDCD), pyruvate carboxylase deficiency, diabetic ketoacidosis, regional hypoperfusion, hepatic disease, shock, sepsis, ethanol toxicity, hemorrhage, hypoxia, hypoperfusion, isoniazid toxicity, phenformin ingestion, metformin ingestion, nucleoside reverse transcriptase inhibitor ingestion, or cyanide ingestion.

14. The method according to claim 1, wherein the compound is of formula II:

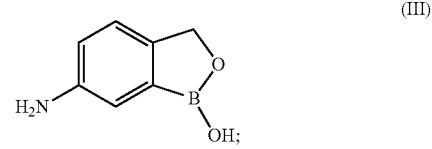

(II)

wherein $R^1$, $R^2$, $R^3$, $R^4$ and $R^5$ are each independently selected from hydrogen, acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$— substituted alkyl, —SO$_2$-aryl, —SO$_2$-heteroaryl and trihalomethyl; and R' and R" are each independently selected from hydrogen, an alkyl, an aryl, substituted alkyl and substituted aryl.

15. The method according to claim 14, wherein the compound is:

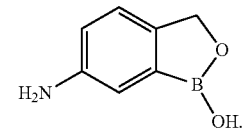

16. The method according to claim 10, wherein an effective amount of the compound is in a range of from 10 µM to 500 mM.

17. A method of treating lactic acidosis in an individual, the method comprising:

administering to the individual a pharmaceutical composition comprising an effective amount of a compound of formula III:

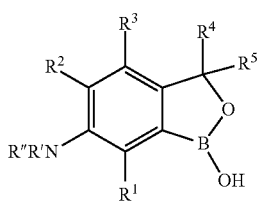

(III)

and determining the blood lactate level of the individual, wherein the boronic acid compound selectively binds to lactate and treats the lactic acidosis.

18. The method of claim 1, wherein $R^1$, $R^2$, $R^3$, $R^4$ and $R^5$ are each hydrogen.

19. The method of claim 1, wherein R' and R" are each hydrogen.

20. The method of claim 18, wherein R' and R" are each hydrogen.

21. The method of claim 14, wherein $R^4$ and $R^5$ are each hydrogen.

22. The method of claim 14, wherein R' and R" are each hydrogen.

23. The method of claim 21, wherein R' and R" are each hydrogen.

* * * * *